(12) United States Patent
Clark et al.

(10) Patent No.: US 7,885,700 B2
(45) Date of Patent: Feb. 8, 2011

(54) ELECTRODYNAMIC SENSORS AND APPLICATIONS THEREOF

(75) Inventors: Terence D. Clark, Lewes (GB); Robert J. Prance, Brighton (GB); Christopher J. Harland, Brighton (GB)

(73) Assignee: The University of Sussex, Brighton (GB)

( * ) Notice: Subject to any disclaimer, the term of this patent is extended or adjusted under 35 U.S.C. 154(b) by 1164 days.

(21) Appl. No.: 10/497,813

(22) PCT Filed: Dec. 9, 2002

(86) PCT No.: PCT/GB02/05560
§ 371 (c)(1), (2), (4) Date: Jul. 5, 2005

(87) PCT Pub. No.: WO03/048789
PCT Pub. Date: Jun. 12, 2003

(65) Prior Publication Data
US 2006/0058694 A1 Mar. 16, 2006

(30) Foreign Application Priority Data
Dec. 7, 2001 (GB) .................................. 0129390.1

(51) Int. Cl.
*A61B 5/04* (2006.01)
(52) U.S. Cl. ....................................................... 600/372
(58) Field of Classification Search ................ 600/372, 600/395; 607/116, 119
See application file for complete search history.

(56) References Cited
U.S. PATENT DOCUMENTS 3,500,823 A * 3/1970 Richardson et al. ......... 600/372
3,568,662 A * 3/1971 Everett et al. ............... 600/384
3,620,208 A * 11/1971 Higley et al. ................ 600/395
3,784,930 A 1/1974 Vosteen et al.
3,870,968 A 3/1975 Vosteen et al.
3,880,146 A * 4/1975 Everett et al. ............... 600/523
3,882,846 A * 5/1975 Fletcher et al. ............. 600/395

(Continued)

FOREIGN PATENT DOCUMENTS

EP 0 551 564 7/1993

(Continued)

OTHER PUBLICATIONS

L. N. Hulley, D. Robson: High input impedance circuits for the measurement of bioelectric potentials Journal of Scientific Instruments, vol. 43, No. 10, Oct. 1996 pp. 728-734.

(Continued)

*Primary Examiner*—George R Evanisko
(74) *Attorney, Agent, or Firm*—Locke Lord Bissell & Liddell

(57) ABSTRACT

An electrodynamic sensor comprises a high input impedance electrometer adapted to measure small electrical potentials originating from an object under test and having a pair of input probes, characterized in that at least one of said pair of input probes has no direct electrical contact with said object, wherein the circuit arrangement of said electrometer comprises an amplifier which includes a combination of ancillary circuits cumulatively to increase the sensitivity of said electrometer to said small electrical potentials whilst not perturbing the electrical field associated therewith.

21 Claims, 18 Drawing Sheets

U.S. PATENT DOCUMENTS

| | | |
|---|---|---|
| 3,967,198 A | 6/1976 | Gensler |
| 4,230,127 A * | 10/1980 | Larson ........................ 600/519 |
| 4,602,639 A * | 7/1986 | Hoogendoorn et al. ...... 600/372 |
| 4,669,479 A * | 6/1987 | Dunseath, Jr. ............... 600/391 |
| 4,801,866 A | 1/1989 | Wixley |
| 5,097,493 A | 3/1992 | Hillen et al. |
| 5,307,818 A | 5/1994 | Segalowitz |
| 6,033,370 A * | 3/2000 | Reinbold et al. ............ 600/595 |
| 6,058,220 A | 5/2000 | Hillen et al. |
| 6,807,438 B1 * | 10/2004 | Brun Del Re et al. ....... 600/372 |

FOREIGN PATENT DOCUMENTS

| | | |
|---|---|---|
| JP | 2002 078693 | 3/2002 |
| JP | 2002 085362 | 3/2002 |
| WO | WO 01/16607 | 3/2001 |

OTHER PUBLICATIONS

M.V. Thomas: "Micro electrode amplifier with improved method of input-capacitance neutralisation", Medical & Biological Engineering & Computing, 1977, pp. 450-454.

R.D. Purves: "High-impedance electronics", Wireless World, Mar. 1983.

* cited by examiner

ELECTRODYNAMIC SENSORS AND APPLICATIONS THEREOF

This invention relates to electrodynamic sensors and applications thereof. These applications span technological fields of great commercial importance such as medical diagnostics, geophysical surveying, biometric sensing and engineering metrology. In particular, the invention may be utilised to derive two-probe electrocardiograms (ECGs), ambulatory electro-encephalograms (EEGs) and the probes for new diagnostic aids such as real-time, three-dimensional displays.

In this specification, the following terms are to be understood to have meanings as indicated below.

Sensor—the complete unit (electrode+electrometer amplifier)

Electrode—the part of the sensor which couples to the signal (e.g. the oxide film electrode)

Electrometer—the electronics (e.g. amplifier including feedback techniques)

Contact mode sensor—no electrical contact, only physical contact

Remote off-body mode—no electrical or physical contact

In order to create a sensitive electrodynamic measuring device it is customary to provide a high input impedance and thereby reduce the power of the input signal required to operate it. However, electronic circuits with a very high input impedance tend to be unstable, so practical devices are usually a compromise between providing the desired input impedance and achieving an acceptable degree of stability. We have devised a method of combining different circuit techniques to achieve several orders of magnitude improvement in sensitivity, whilst still maintaining sufficient stability to permit a relatively unskilled operator to make measurements in everyday conditions.

According to the present invention there is provided an electrodynamic sensor comprising a high input impedance electrometer adapted to measure small electrical potentials originating from an object under test and having a pair of input probes, at least one of which has no direct electrical contact with said object, wherein the circuit arrangement of said electrometer comprises an amplifier which includes a combination of ancillary circuits cumulatively to increase the sensitivity of said electrometer to said small electrical potentials whilst not perturbing the electrical field associated therewith.

According to a particular aspect of the invention there is provided an electrodynamic sensor for biometric measurements including a high input impedance electrometer having a pair of probes for the detection of small electrical potentials originating from potentials originating from a body under test wherein there is no direct electrical contact between at least one of said pair of probes and said body. Advantageously, said apparatus may be used for the measurement of electrocardiograms, electro-encephalograms or electro-oculograms.

The invention will now be particularly described with reference to the accompanying drawings, in which.

A high impedance electrometer based on the present invention incorporates a complex combination of circuit techniques. It employs a number of separate components, some of which may be found in commercial laboratory electrometers.

Figure 1:
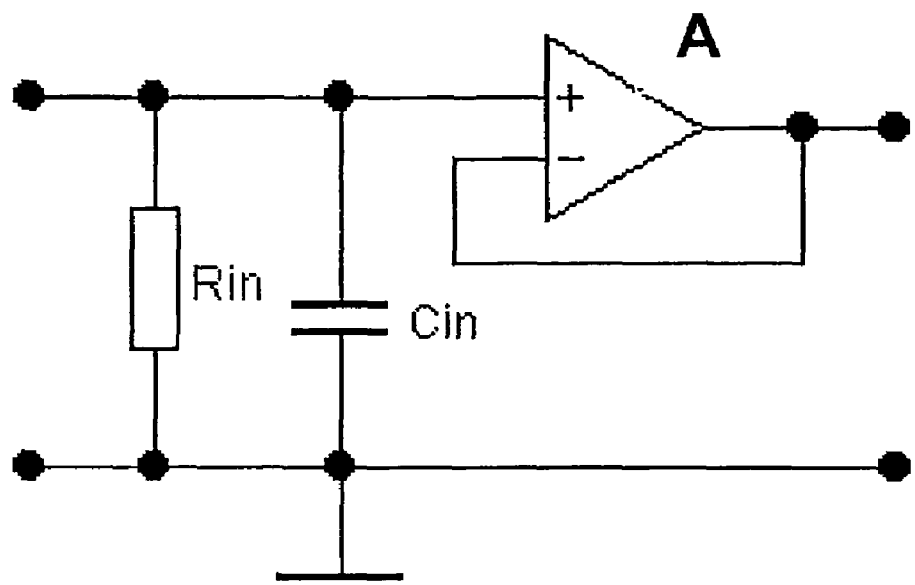
FIGS. 1 to 9 are explanatory circuit diagrams illustrating features of the invention.

Taking a real amplifier to be a perfect amplifier A plus finite input resistance ($R_{in}$) and input capacitance ($C_{in}$) this gives the arrangement shown in FIG. 1, where $R_{in}$ and $C_{in}$ may be regarded as internal (intrinsic) limits due to the performance of the amplifier. The closed loop gain is assumed to be equal to one.

Figure 2:
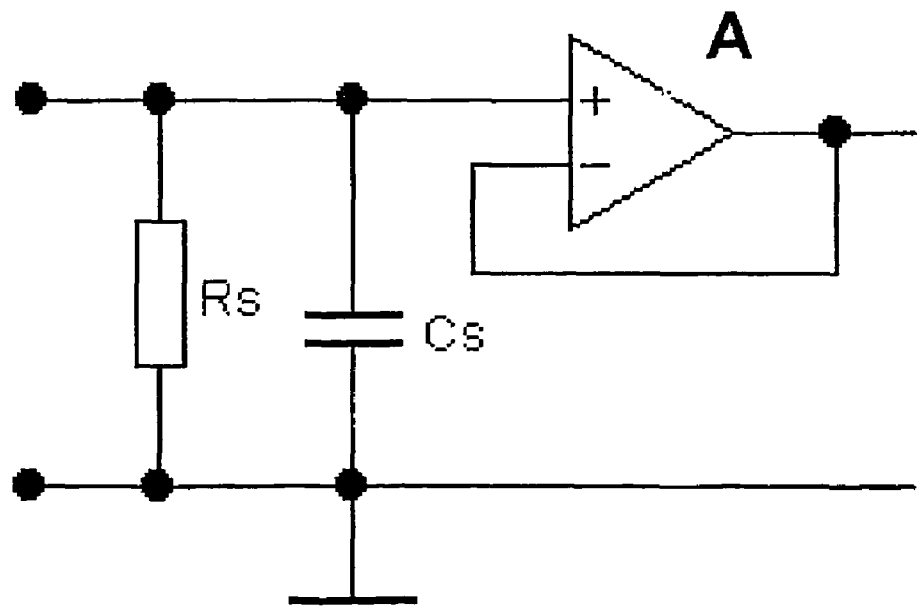
Figure 3:
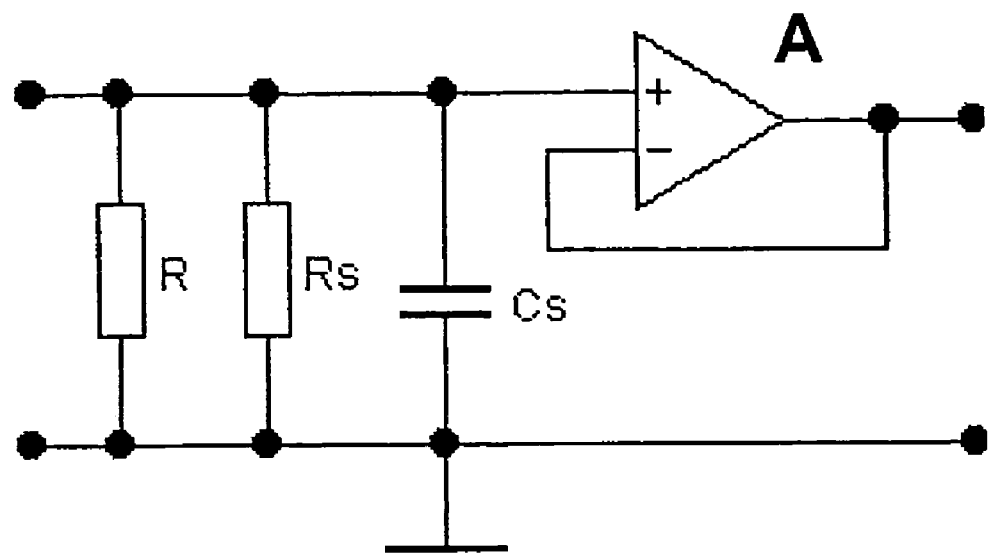

In a practical circuit, the device typically incorporates some form of printed circuit board with input cabling etc., in order to operate. These will introduce another capacitative term $C_s$ and possibly a parallel leakage term $R_s$. The circuit is re-drawn (FIG. 2) putting $R_{in}$ and $C_{in}$ within the amplifier;

In practice $R_s$ may usually be neglected as very high (almost open circuit). In this case, the resistive contribution to the total input impedance is dominated by the requirement to provide a steady input bias current to the amplifier. This ensures that a stable dc operating point can be maintained. Hence the minimum requirement for a stable circuit would be the inclusion of a fixed input resistance R. (FIG. 3)

With modern low input bias current amplifiers, the bias requirement $I_b \sim 100$ A, giving an offset voltage ($V_{off}$) of;

$$V_{off} = I_b \times R \quad \text{(Eqn. 1)}$$

Typically, $V_{off} = 100 \text{ fA} \times 100 \text{ G}\Omega = 100 \text{ mV}$ The use of input bias resistors >100 GΩ (if available or practical) results in offset voltages of many volts with associated problems of thermal drift due to the poor temperature coefficient of such resistors. This has always presented a problem for conventional electrometers.

Nevertheless a high resistance component is still required. This usually takes the form of a 100GΩ resistor but may be an alternative component such as a low leakage diode, for example Siliconix PAD1, a small neon lamp coupled to a suitable source of illumination (to control the resistance) or the channel of a field-effect transistor.

The input impedance of the amplifier is advantageously enhanced by a combination of feedback techniques.

Figure 4:
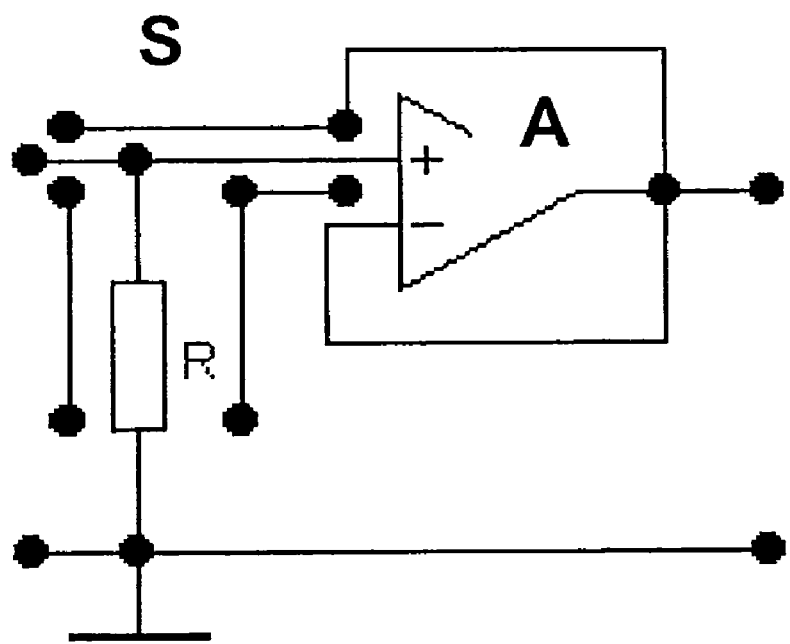

One technique which gives improved operation is guarding. (FIG. 4) This is a positive feedback technique which involves physically surrounding the input circuitry, wiring and electrode as completely as possible with a shield S driven by the output of the amplifier. Charging effects on the capacitance are alleviated by maintaining the same potential (signal potential) on the shield as on the input electrode, thus removing the stray component $C_s$. In practice, this is not perfect but produces a reduction of the order of $1/A_0$ where $A_0$ is the open loop gain of the amplifier.

Figure 5:
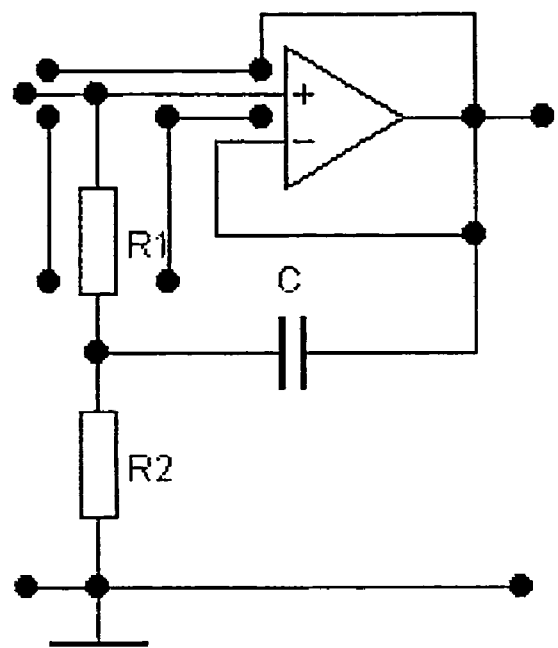

Bootstrapping may then be applied to a component in order to increase the effective impedance at the signal frequency. (FIG. 5) This is also a positive feedback technique. By splitting the bias resistor R into two components R1 and R2, a capacitor C is utilised to apply the output voltage to the mid point, see FIG. 5. Thus the input voltage appears at both terminals of the upper resistor, resulting in zero current flow and an infinite impedance. In practice, there is a small error, again associated with the open loop gain, but also with the attenuation caused by $R_2$ and the $CR_2$ time constant. The latter prevents the bootstrapping from operating below the frequency associated with this time constant.

Figure 6:
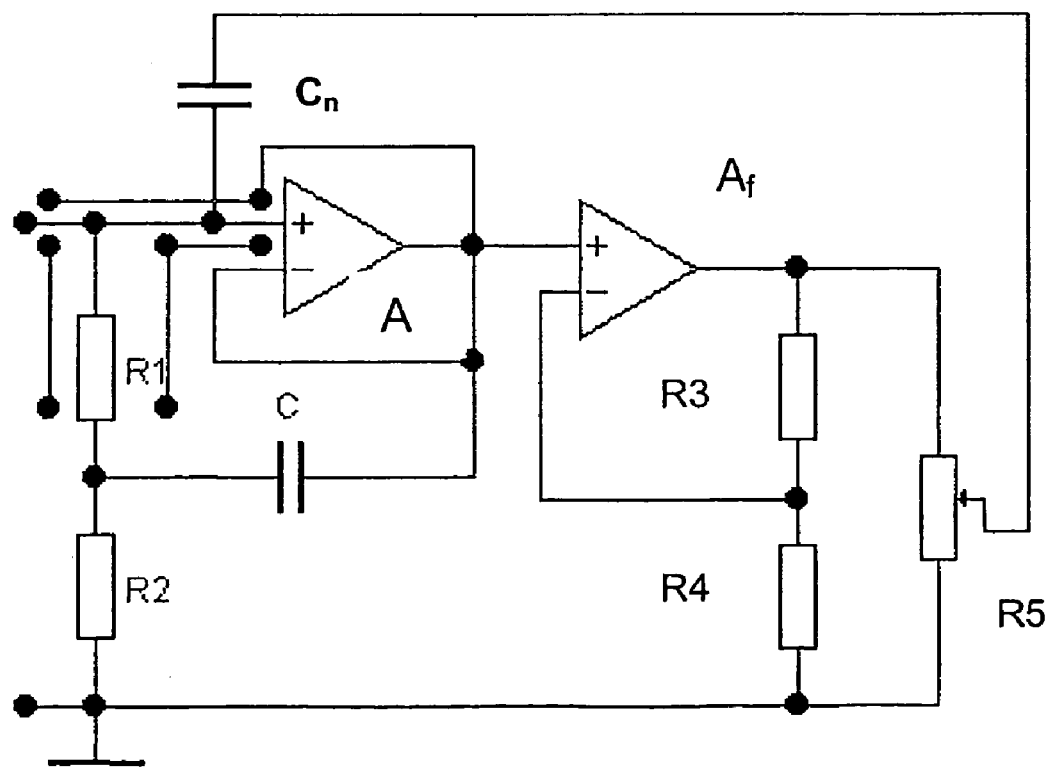

Another positive feedback technique is neutralisation, which may be used to address the intrinsic input impedance of the amplifier. (FIG. 6) A small capacitor $C_n$ (usually<1 pF) is used to introduce the output signal directly to the input. Resistors R3 and R4 and potentiometer R5 are used to set the neutralisation to a desired level. With a carefully controlled and fixed geometry for the input electrode and guarding structure this permits $C_{in}$ to be reduced by a factor $\sim 1/A_0$.

The results of these stabilisation techniques may be summarised by the following table.

TABLE 1

| Bare biased circuit | plus Guarding | plus Bootstrapping | plus Neutralisation |
|---|---|---|---|
| $R_{in} \sim 10^{14} \Omega$ | $10^{14} \Omega$ | $10^{14} \Omega$ | $10^{17} \Omega$ |
| $C_{in} \sim 3pF$ | 3pF | 3pF | $10^{-15}F$ |
| $R_s \sim 10^{18} \Omega$ | $10^{18} \Omega$ | $10^{18} \Omega$ | $10^{18} \Omega$ |
| $C_s \sim 10pF$ | $10^{-15}F$ | $10^{-15}F$ | $10^{-15}F$ |
| $R \sim 10^{11} \Omega$ | $10^{11} \Omega$ | $10^{17} \Omega$ | $10^{17} \Omega$ |

In an alternative embodiment, optical feedback stabilisation loops are used instead of a dc negative feedback loop. In this arrangement, a low-leakage photodiode or a small neon lamp is coupled to a suitable source of illumination (to control the resistance) in place of the input resistor R.

In a still further embodiment, a field-effect transistor channel is used as a gated resistor to implement stabilisation.

In order to achieve maximum sensitivity, it is desirable to stretch each feedback technique to the limit by employing a defined geometry for the input circuitry and by combining all three techniques. This procedure is totally unconventional as it contravenes established practice. To use these positive feedback techniques in combination in one amplifier would be expected to create instability in operation.

Associated with this approach, a further step may be employed to achieve the goal of extracting the maximum benefit from the combination of positive feedback techniques. The principal problem with increasing the level of positive feedback is that instability occurs, leading to either oscillation, or more usually, dc drift until the amplifier saturates at the supply rail voltage.

Figure 7:
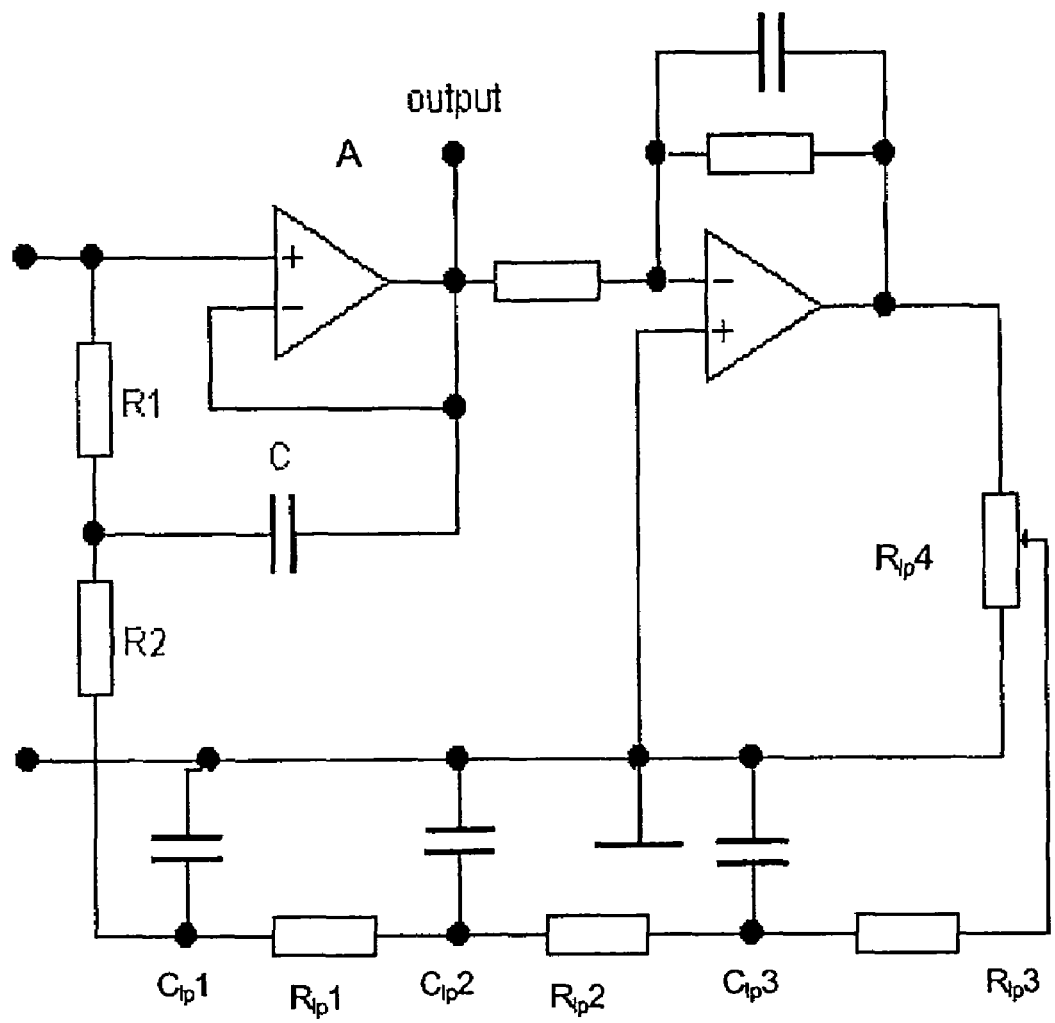

Preferably, this problem is solved by introducing a dc to low frequency negative feedback loop $C_{lp}1$, $R_{lp}1-C_{lp}3$, $R_{lp}3$ to stabilise the dc operating point of the system by amplifying the output voltage, using low pass filter circuits to remove all signal frequencies, and feeding this filtered signal into the input bias resistor network (i.e. at $R_2$). This is shown in FIG. 7, in which the guarding and neutralisation circuitry has been omitted for clarity.

The net result is a system with extreme input impedance, $\sim 10^{17} \Omega$ in parallel with $C \sim 10^{-15}F$, which is stable at dc when operated open circuit at the input electrode (i.e. in the limit of weak capacitive coupling to a source).

This technique is so effective that it is possible to introduce significant gain into the first stage electrometer amplifier. This would usually produce extreme instability, but with the feedback loop in place in the amplifier it is stable and produces large reductions in the noise referred to the input. Typically a gain of ×10 will reduce the noise floor by ×10, a gain of ×100 will reduce the noise floor by ×30. Such reductions in noise are only possible with large gain, which itself is only possible using a feedback technique applied to the bias network as described above.

A further arrangement for providing the input bias current has presented itself as the result of a serendipitous discovery. If an amplifier is operated without provision for dc bias at the input, then the output will drift until it saturates on a supply rail ($V^+$ or $V^-$). This may be either positive or negative. It is usual practice to bias amplifiers with symmetric voltages i.e. $V^+=V^-$. However, by biasing asymmetrically, it is possible, in many instances, to reverse the direction of the drift. The mechanism for this is believed to be that the input bias current is balanced by on-chip leakage currents which are manipulated using the supply rail voltages. If the correct voltage asymmetry is chosen this gives a stable dc operating condition without using a bias component on the input. In order to ensure that the stable operating condition is maintained, a dc feedback loop which responds to the drift at the output of the amplifier is incorporated into the power supply system. The direction in which the supply rails move in order to counteract the drift may be selected by the man skilled in the art according to the specific amplifier chosen. The feedback amplifier $A_f1$, $A_f2$ may be either inverting or non-inverting as appropriate. The error (offset) signal is amplified and added to the normal $V^+$ and $V^-$ supplies.

Supply modulation (the bootstrapping of device capacitance) may be used as an alternative to neutralisation to reduce input capacitance ($C_{in}$).

Figure 8:
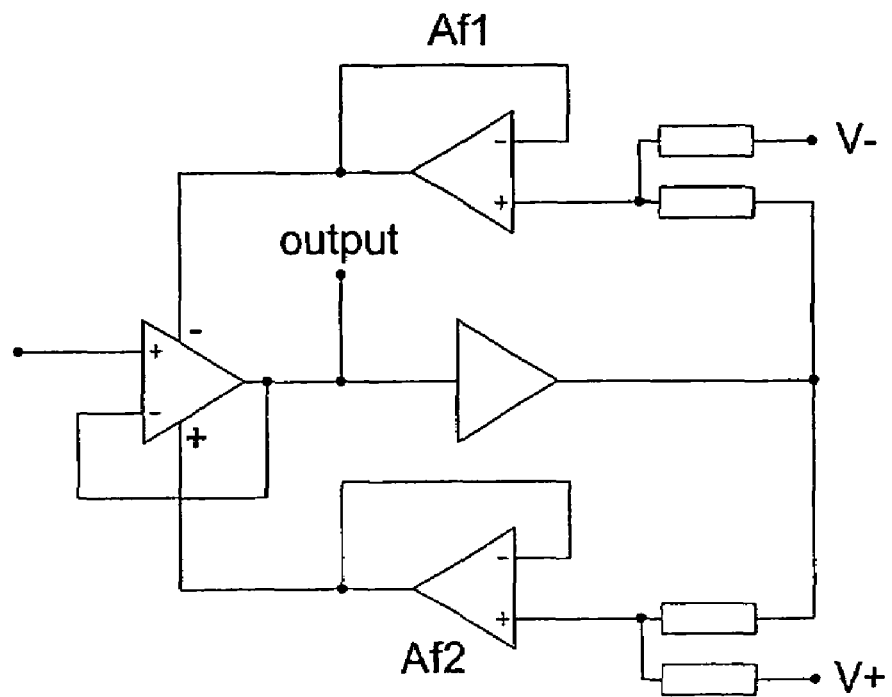

No filtration is shown in FIG. 8. Only dc to low frequency signals would be fed back in negative feedback to stabilise the electrometer. This technique may also be used to add (i.e. positive feedback) the signal to the supply rails (supply modulation) as an alternative implementation to neutralisation. In this mode the device (input) capacitance is effectively eliminated by bootstrapping the active input components of the amplifier.

Figure 9:
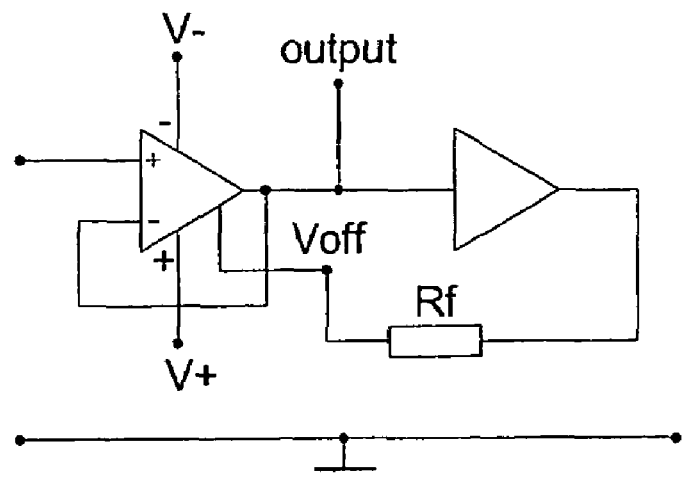

An alternative implementation for this scheme is to introduce the offset correction signal $V_{off}$ via the offset voltage adjustment pin (offset null) of the integrated circuit chip. The exact configuration will depend on the amplifier chosen but, in general, would have the configuration shown in FIG. 9 in which, as in FIG. 8, all other feedback circuits have been omitted for clarity.

The sign of the feedback amplifier depends on the particular amplifier and is selected to ensure negative feedback.

Both positive and negative feedback may be used for supply modulation. Positive feedback with a high pass filter may be used as an alternative technique to neutralisation. Negative feedback may be used with low pass filter/integrator as an alternative to the dc feedback stabilisation loop.

Electrodynamic sensors incorporating these circuit enhancements find particular application in sensing electrical activity of the human body. They permit probes to be in physical contact with the human body whilst maintaining non-invasive, electrically isolated operation. The use of these probes in the novel sensors allows electrical activity in the human body to be monitored at high resolution with low noise contribution. One particular application is the production of high-resolution electrocardiograms and remote sensing of human heart activity at distances of up to 1.0 m from the body.

Spatio-temporal potentials on the surface of the human body are routinely monitored for medical diagnostic purposes by the application of electrical probes to the body. For the monitoring of the electrocardiogram (ECG), metal electrodes are customarily applied to the skin with adhesive pads and a silver chloride gel is used to act as an electrical transducer to convert the ionic current flow in the surface skin into a signal which can then be detected by an electronic amplifier. High-resolution ECGs which are required for precise diagnostic purposes, where, for example, the identification of the His- Purkinje discharge is important in time relation to the atrial and ventricular depolarisations, can generally only be acquired using intra-cardiac techniques where the biosensor is inserted into an artery via a cardiac catheter.

The monitoring of electrical activity from the human brain to produce an electroencephalogram (EEG) has hitherto required multiple electrical connections to the scalp often resulting in the removal of hair and epidermal tissue. EEGs which can be identified from localised parts of the brain often require subcutaneous wire probes to be inserted into the patient. The techniques in current use for the monitoring of human electrical activity have direct electrical contact with the body with a corresponding current being drawn from the source (body). In this situation there will always be the possibilities of source potential modification, measured signal distortion and patient electrical shock. The development of a truly non-invasive method of sensing human body signals has many advantages over the restrictions imposed by the techniques in current use, especially in relation to the comfort of the patient.

High input impedance electrodynamic sensors in accordance with the present invention enable human body electrical activity to be monitored using non-invasive, electrically isolated probes using either a contact mode (physical contact, electrically isolated) or a remote off-body mode (no physical contact).

For efficient signal transfer from the body to the first stage of the electrometer amplifier a capacitive coupling is used. In the case of the remote (off-body) probes this capacitance is defined by the air gap between the body being measured and the sensor (typically a disc of 25 mm to 200 mm in diameter) and is modified slightly by any material, such as clothing, which may be in the air-gap space. The coupling capacitance in the remote mode is typically less than 1 pF. Increased input impedance and reduced effective input capacitance of the electrometer amplifier results in more efficient coupling and hence a larger signal-to-noise ratio. Preferably, these remote electrodynamic sensors utilise the feedback and guarding techniques described previously. For the contact probes a strongly capacitative (large capacitance) coupling electrode is used to make, physical contact with the body being measured.

In an alternative embodiment, a large capacitance (>100 nF) is used to couple the body being measured to an electronic amplifier. This gives two advantages over the remote mode. First, the strong coupling reduces or eliminates signal attenuation due to the input capacitance of the amplifier and second, the effective source impedance (the impedance that the amplifier input sees as it looks into the source) is reduced, thereby reducing the current noise contribution of the amplifier. The large capacitance required (and electrical isolation) is produced by using a disc electrode with a thin film of insulating material on the contact surface. The thickness is chosen to provide the capacitance required, given the sensor surface area and sensor disc material (substrate). Typically, the thickness is of the order of 1 μm. We have used anodised oxide films but sputtered and evaporated films may be utilised in alternative embodiments. Suitable materials are $Al_2O_3$, $Nb_2O_5$, $Ta_2O_5$ and, most commonly, $TiO_2$. In general, oxide, nitride or another film with a high dielectric constant may be used. If $SiO_2$ is used, this will enable the electrometer to be fabricated on the same substrate disc of silicon. The thin-film sensor (FIG. 10) is incorporated into an assembly with an electrical guard electrode and electronic amplifier to produce a complete active probe. This incorporates a sensor electrode disc 1 having a surface oxide layer 3 on a substrate 5, connected by a lead having a guard 7 to an amplifier 9.

Figure 10:
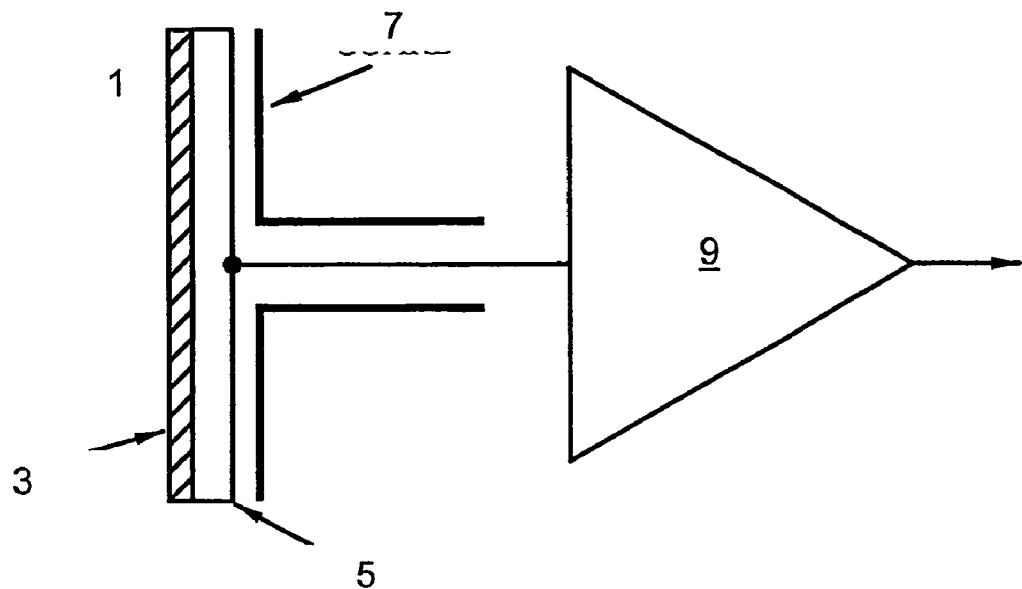
FIG. 10 is a sensing probe used in a specific embodiment of the invention.

FIG. 10 depicts a diagram of a typical active sensor probe for contact mode body electrodynamic measurements. An oxide layer is fabricated on the electrode substrate to form a capacitor which provides strong electrical coupling.

Biosensor probes for electrodynamic body sensing may alternatively be used in an electrically isolated contact sensing mode or a remote sensing mode. Preferably, the contact mode uses single or multiple probes where signal coupling is made via specially developed sensors. The remote mode preferably uses a fixed sensor which forms a capacitive coupling to the body under measurement. By applying feedback networks to a low-noise field-effect transistor input amplifier the effect of the bias requirements is reduced, the input resistance is increased and the input capacitance is lowered to match the amplifier to the signal source efficiently. This results in minimum loading of the source and low-noise operation. Recent work with coupling the latest generation bio-sensors to the electrometers has produced input referred noise levels down to 100 nV/√Hz at 1 Hz for contact mode operation.

Figure 11:
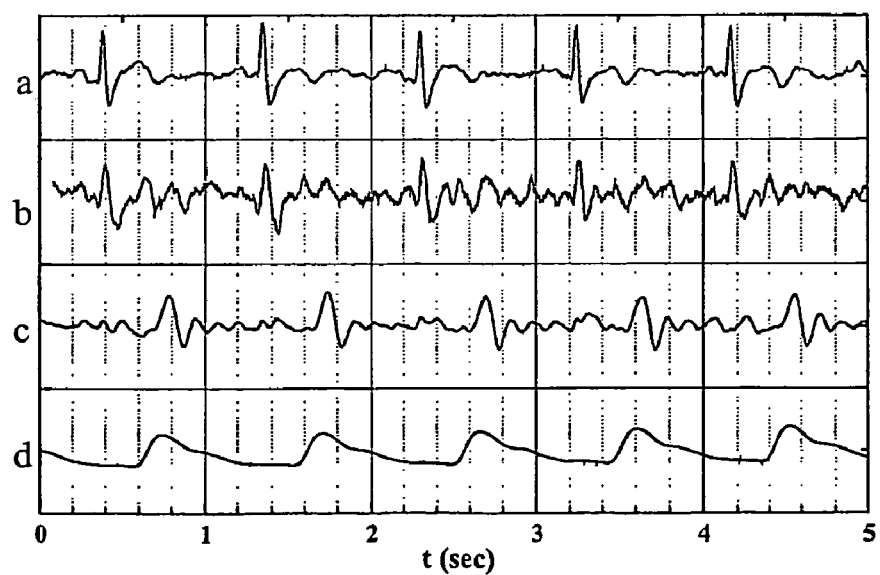
FIGS. 11 to 20 show measurements taken with an electrodynamic sensors in accordance with specific embodiments of the invention

An example of the application of the sensor probes to time domain monitoring of human body electrical activity is shown in FIG. 11. FIG. 11a shows a high-resolution ECG detected from the tip of the right-hand fore-finger using a single, electrically insulated, non-invasive, contact probe. A corresponding ECG remotely detected at a distance of 5 cm from the chest (through clothing) is shown in FIG. 11b. FIG. 11c shows a signal corresponding to the arterial pulse which was remotely detected at a distance of 30 cm from the chest (through clothing). FIG. 11d is a time reference signal derived from a commercial saturated oxygen pulse oximeter. (Signal bandwidth (a-c)=2 Hz to 30 Hz)

Figure 12:
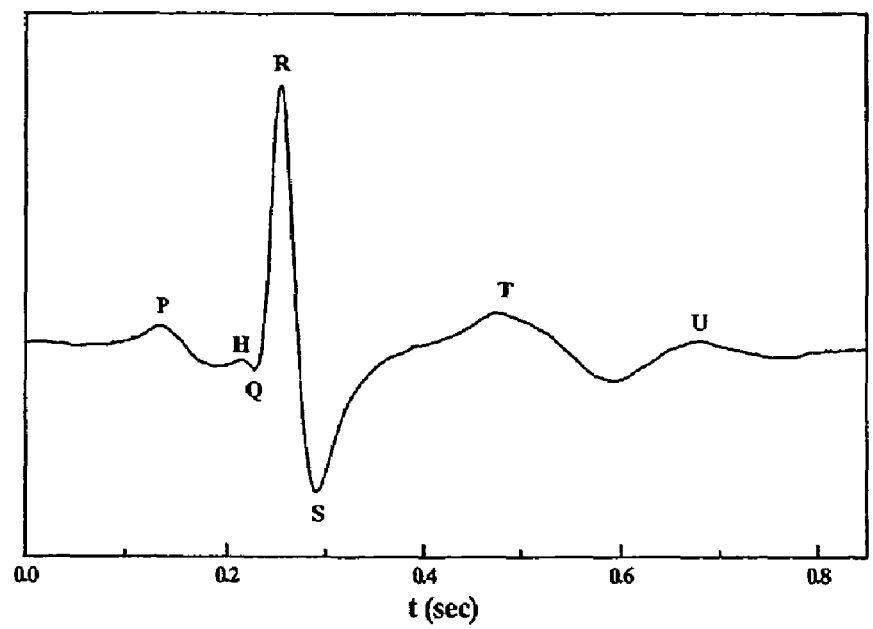

The fidelity of a single probe ECG will be limited by electromyographic and skeletal body noises which can be largely eliminated by using a differential signal from two probes. FIG. 12 shows an example of a high-resolution electrocardiogram (HR-ECG) recorded from the tips of the fore-fingers using a pair of the new electrically-insulated, non-invasive, contact probes. The ECG in FIG. 12 is equivalent, in cardiology terminology, to the 'I' lead where the signal is derived from the difference between the two arm leads ('LA'-'RA'). In this case the 'I' lead is derived from the difference between the left and right finger signals. The ECG shows the usual character of a high-resolution ECG, i.e. the P wave, the QRS complex and the T wave. The tips of the fore-fingers of each hand were simply placed on to separate biosensors and the differential signal (left-right) was displayed. The differential signal (left-right) shows the usual characteristics of an HR-ECG, i.e. the P wave, the QRS complex and the T wave. In addition, this HR-ECG shows features which correspond to events less likely to show up in a conventional 3-lead or 12-lead ECG—peaks corresponding to the positions of the His-Perkinje discharge (H) and the U wave.

Figure 13:
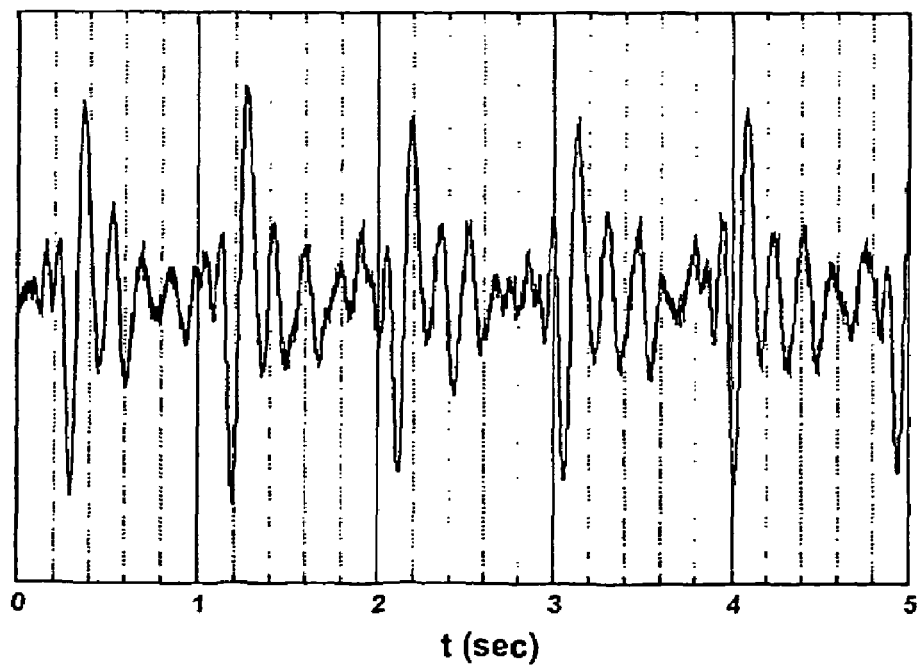

Using remote biosensors in accordance with a particular embodiment of the present invention, the human heartbeat has been detected at distances of up to one meter away from a clothed body. By arranging a pair of remote sensors one meter apart, with the human body in between the sensors, a signal corresponding to the arterial pulse is detected, as shown in FIG. 13.

Multiple sensors, arranged into linear or higher dimensional areas may be used to produce dynamic potential line profiles or maps which measure and display the electrical activity on the surface of a body or from internal body organs. For example the ECG signal can be detected simultaneously from a number of sensors arranged in an area array (x,y) in contact with the surface of the chest. These ECG signals can then be used to provide a real-time dynamic display of the electrical potential over the area x,y which, in the case of the ECG shows a dynamic picture of the electrical activity in the heart—the heart working. When remote off-body sensor arrays are used the display is similar but will have the distance and angular information to enable the source of the electric activity to be determined using an inverse transform technique. A combination of contact and remote off-body sensor arrays may be used to produce electrodynamic maps from different areas on the surface of the body and at different depths within the body tissue.

The scalable nature of this technology permits operation with a wide range of coupling capacitance between the sensor and the source of the signal. This means that the probe may have a wide range of stand-off distances from the surface of the sample being measured. For example, a sensor may be used to acquire electrodynamic maps from above the surface of an active integrated Circuit. A single probe may be scanned over the surface to acquire the data in, for example, a raster scan pattern. Alternatively an array of sensors may be used to acquire data simultaneously. Single probes or multi-dimensional arrays may be scanned across a surface to provide a significant reduction in the data acquisition time. Likewise a single or multi-dimensional array may be used to acquire data simultaneously in real time without the requirement to move either the sensors or the sample.

It should be noted that although guarded electrode structures are typically coaxial in nature, they may take other forms, particularly with microprobes. The objective is to provide the most complete guarding possible. With miniaturised thin film electrodes, one embodiment will be a planar tri-plate configuration, with the measurement electrode sandwiched between two guard planes.

Figure 14:
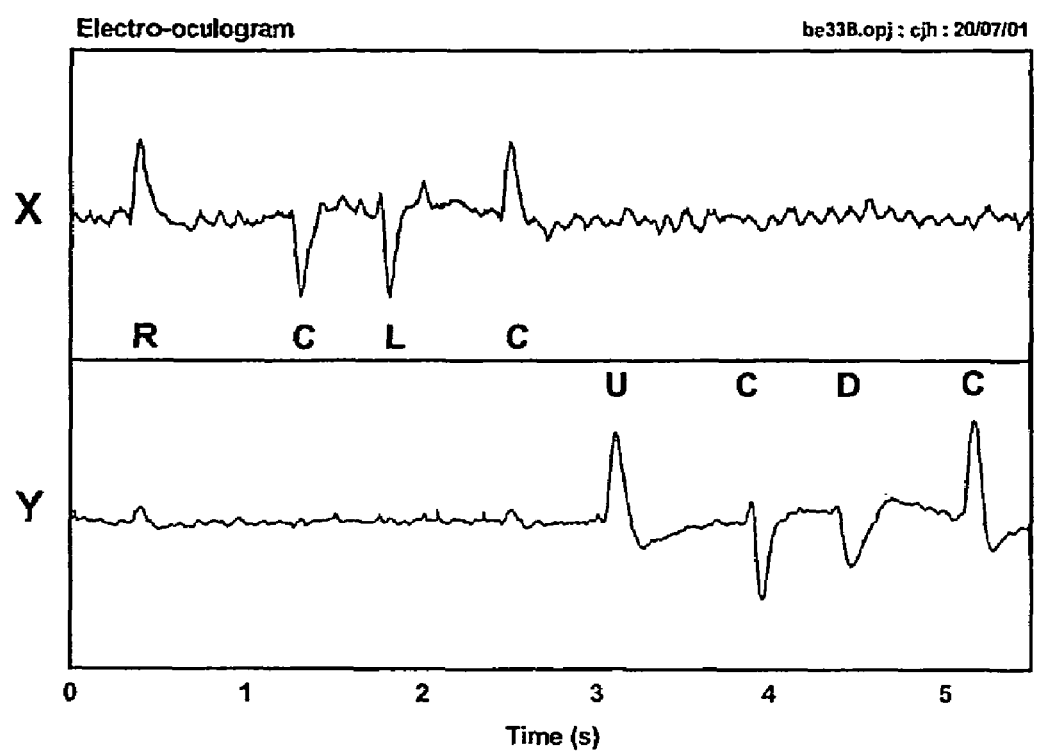
Figure 15:
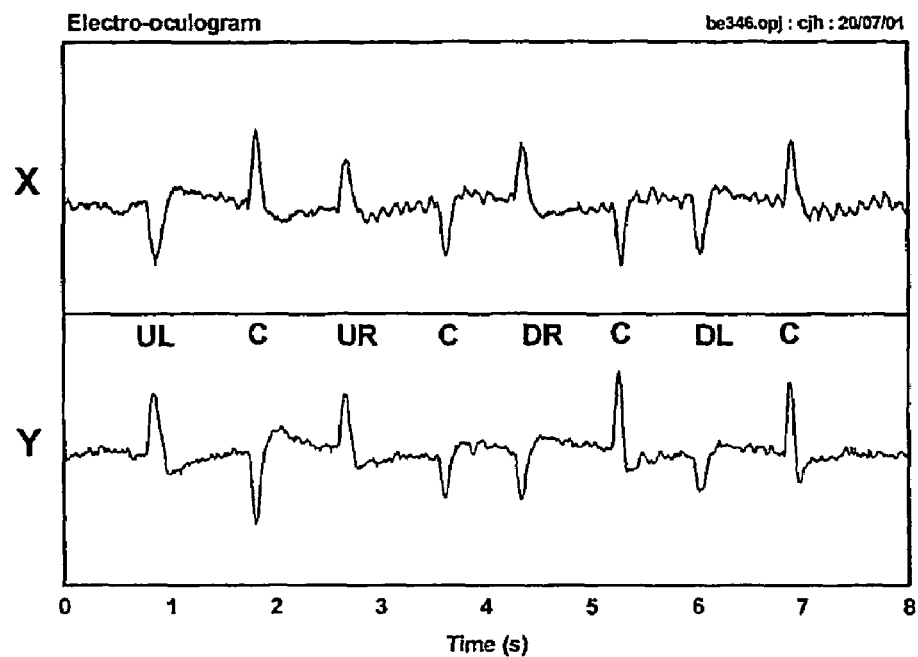
Figure 16:
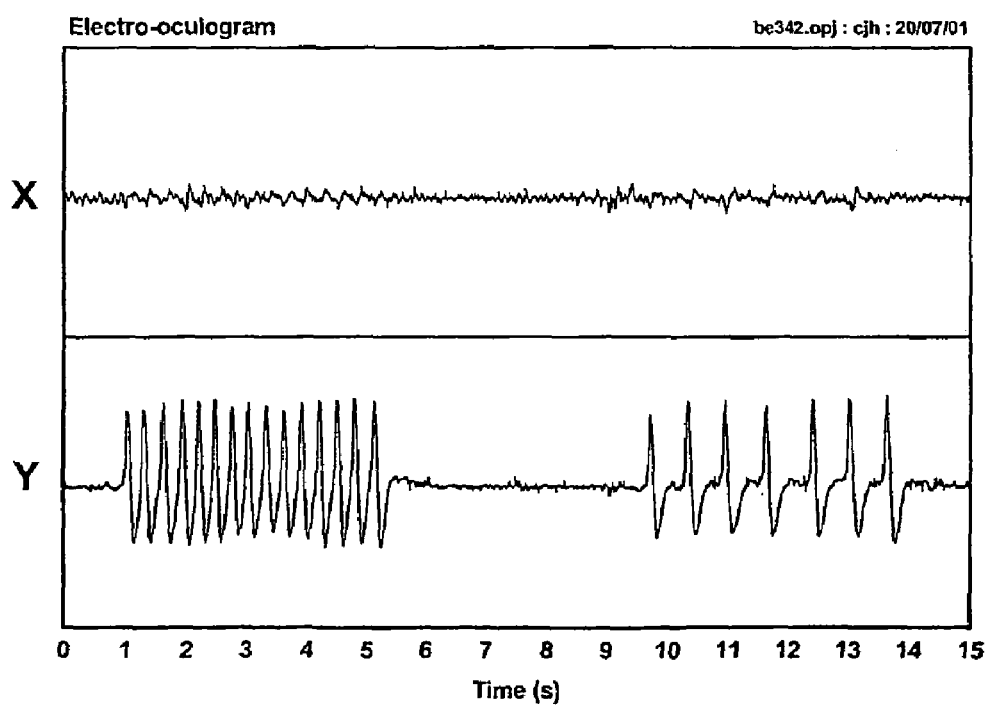

Further embodiments of the invention enable human body electrical activity to be monitored using non-invasive, electrically isolated, and in some cases, non-contact sensors. The signals that may be measured include the electrocardiogram (ECG) and electroencephalogram (EEG) and the electro-oculogram (EOG). In present practice, the EOG is monitored using electrodes which are placed around the eye, either being inserted under the skin or in electrical contact with skin via an electrolytic paste. We have used four sensors, one pair to detect the left-right eyeball movement and one pair to detect the up-down movement. Electrodes are preferably positioned on the front temple lobes, above and below the eyes. The EOG sensors are in dry, physical contact with the surface of the skin and are electrically insulated from the body. FIGS. 14-16 show examples of the use of these sensors for measuring the deflections of the corneo-retinal potential as the eyeball moves with respect to the head. In the examples shown the angular movement of the eye is approximately ±20°.

FIG. 14 shows EOG signals from X and Y sensors showing voltage deflections resulting from left and right, and up and down eye movements (R=right, L=left, U=up, D=down and C=centre). FIG. 15 shows EOG signals from X and Y sensors showing voltage deflections resulting from diagonal eye movements (UL=up left, UR=up right, DR=down right, DL=down left and C=centre). FIG. 16 shows EOG signals from X and Y sensors showing voltage deflections resulting from two separate periods of repetitive blinking of the eyes.

In a still further embodiment, an EEG from the posterior of the brain in the region of the occipital lobe is monitored. In this embodiment, the sensor probe used was of a hand-held differential input type using two sensors each of 25 mm diameter. The sensors made physical, but not direct electrical, contact to the surface of the head and no special preparation was made to the scalp, the signals being collected through the hair. The sensors were placed approximately in the 'P3' and 'O1' positions referring to the international standard '10-20' system. Preferably, a non-allergenic, aqueous non-electrolytic gel is used to reduce static noise from the hair (triboelectric effect) and to enhance the coupling because it is chemically inert and has a high dielectric constant.

Figure 17:
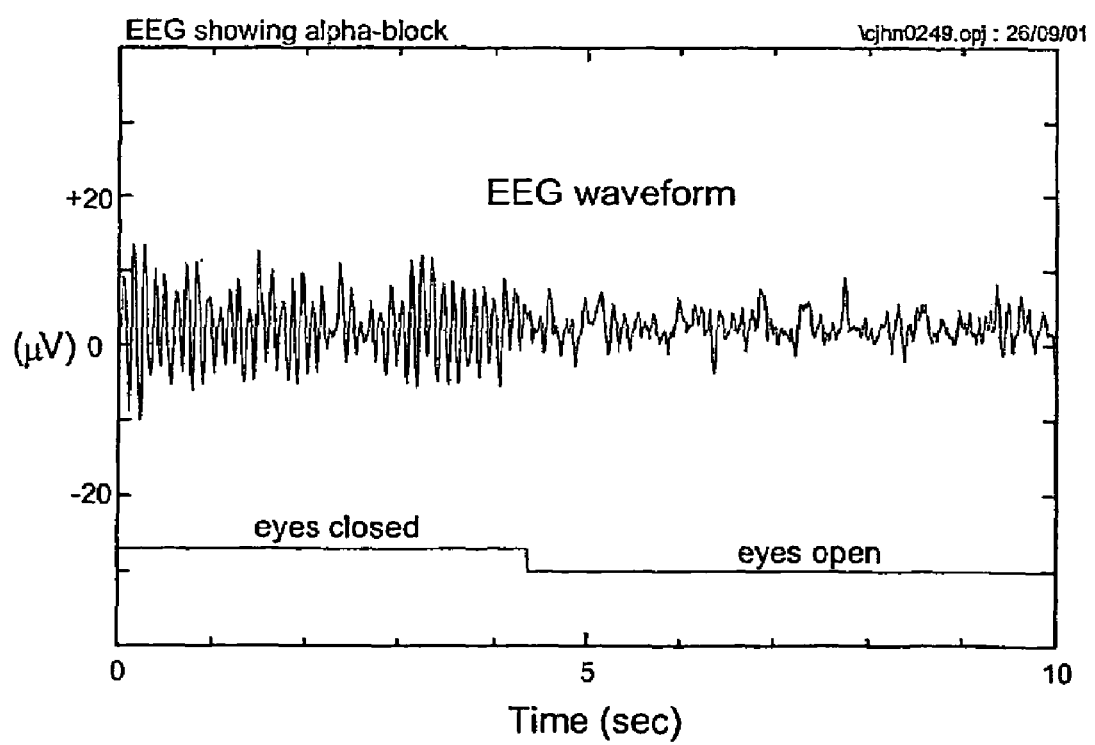

FIG. 17 is a time domain signal of 10 sec of EEG data collected from the surface of the head in the posterior region. The EEG waveform to the left shows the alpha-wave which is present when the subject's eyes are closed but is 'blocked' when the eyes are opened.

Figure 18:
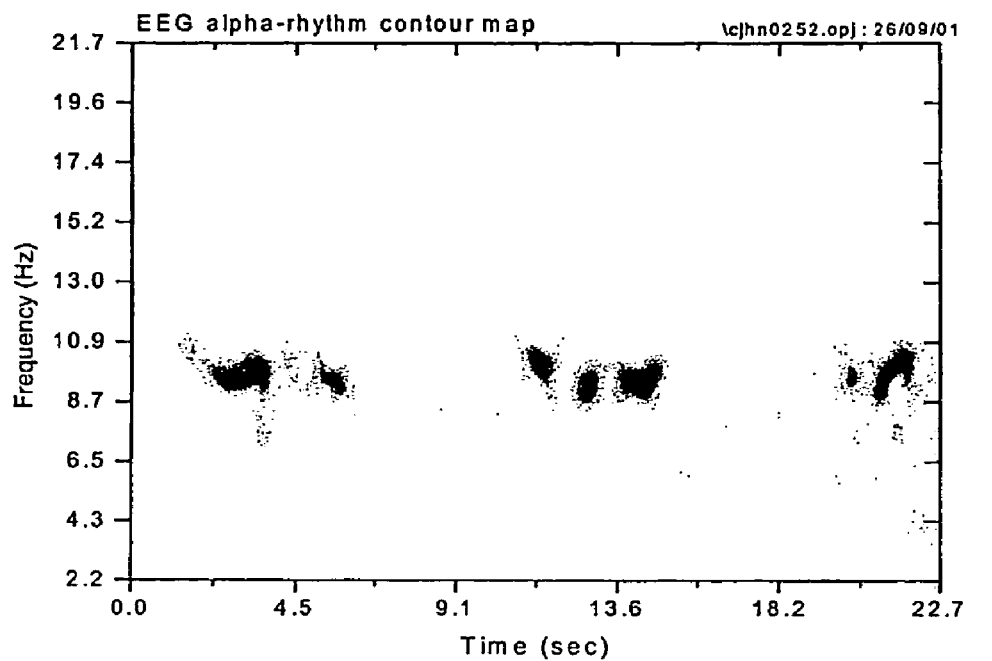
Figure 18:
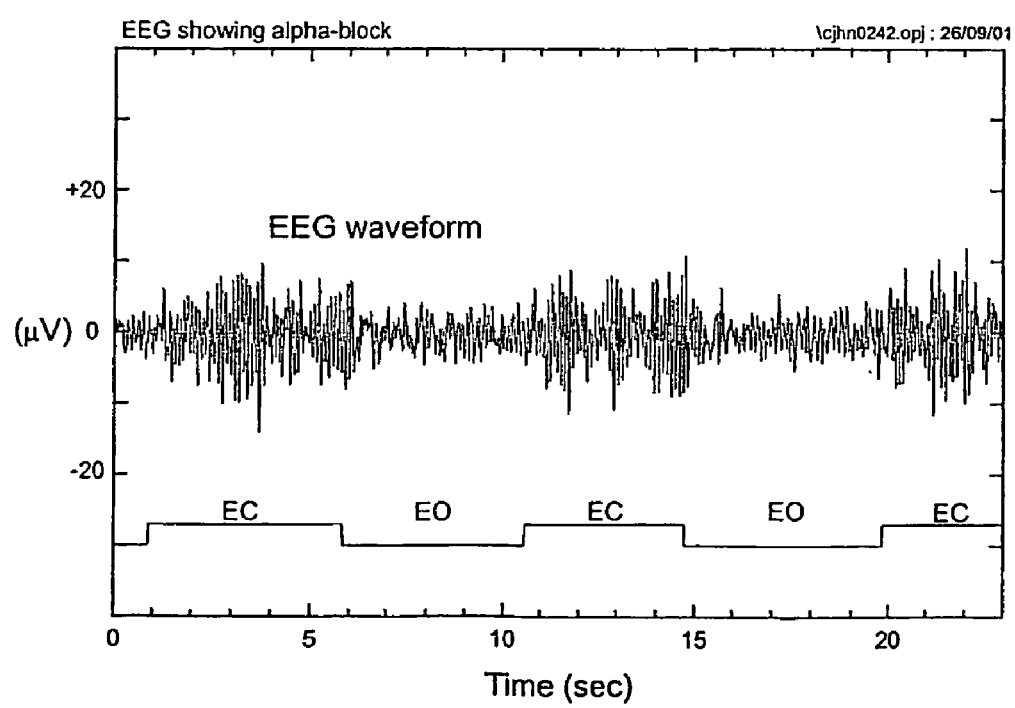

FIG. 18 is an EEG waveform collected through hair from the posterior of the head showing alpha-blocking. The bottom window shows approximately 23 sec of EEG data together with an event marker which shows the state of the subjects eyes (EC=eyes closed, EO=eyes open). The changes in the amplitude of the EEG waveform as the eyes are opened and closed can clearly be seen. The top window is a joint time frequency (JTF) plot for the same EEG data showing that during the eyes closed period the EEG consists predominantly of an alpha-wave of approximately 10 Hz which disappears when the eyes are opened.

Figure 19:
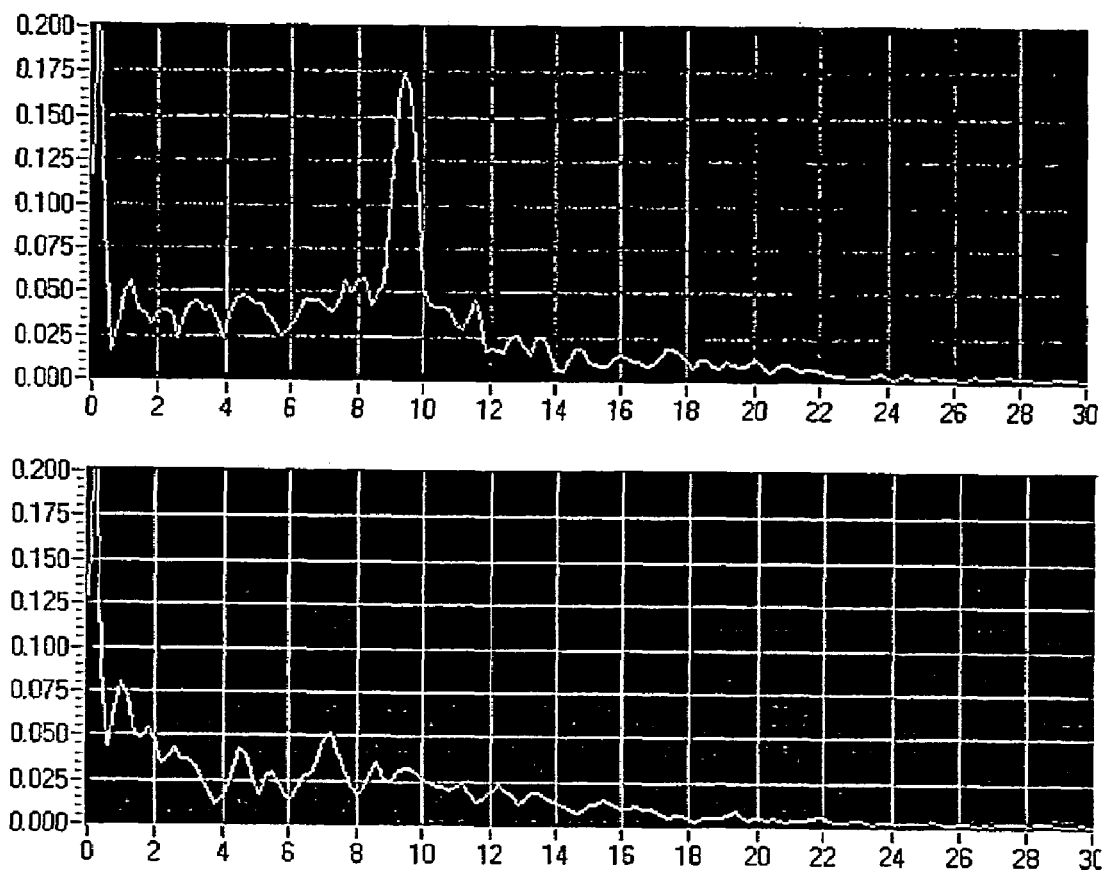
Figure 20:
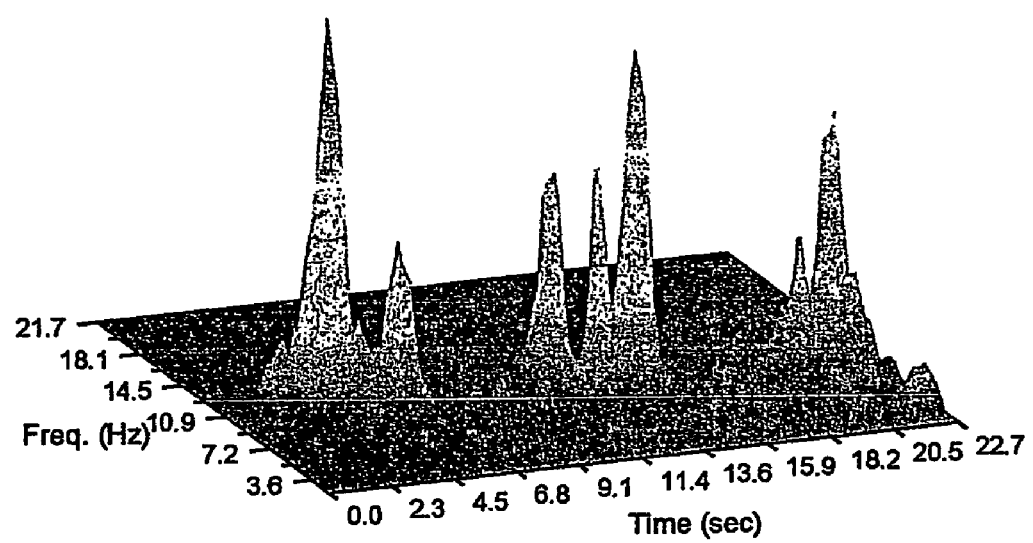

FIG. 19 shows power spectra corresponding to the EEG waveforms of FIGS. 17 and 18. The top power spectrum relates to the 'eyes closed' period and the lower power spectrum relates to the 'eyes open' period. The data shows an (alpha-rhythm) peak at approximately 10 Hz during the 'eyes closed' period which disappears when alpha-blocking occurs when the eyes are opened. X-axis is frequency in Hz. FIG. 20 is a Joint Time Frequency plot of the EEG waveform of FIG. 18 plotted as a three-dimensional colour map. This shows the predominantly 10 Hz alpha-rhythm occurring during the period when the subjects eyes are closed and disappearing when the eyes are opened.

It is well known that the alpha-rhythm (8-14 Hz) is most prominent when the subject is at rest with the eyes closed. When the eyes are opened the alpha-rhythm usually disappears being replaced by beta rhythms (14-35 Hz)—a phenomenon called alpha-blocking. The observation of this alpha-blocking indicates that the EEG is in fact being monitored.

In a further specific embodiment, wrist-mounted electrodynamic sensors are used to achieve high resolution ambulatory electrocardiographic monitoring. A high resolution electrocardiogram can be acquired using two of these sensors mounted wristwatch style, one on each wrist. These sensors, which do not require a real current conducting path in order to operate, are used non-invasively without making direct electrical contact to the subject. In addition to their high resolution capability, these sensors have major advantages over current, wristwatch style, heart rate monitors used in the health and fitness fields. Furthermore, their sensitivity and low noise floor have made it possible to detect a peak which corresponds, in timing, to the His bundle depolarisation—a feature not normally seen in conventional surface electrocardiograms. These new devices find particular application in clinical medicine, as well as in sport and ambulatory monitoring.

A standardised connection scheme has been developed for the electrocardiogram because it is routinely used in clinical environments for diagnosis, (see Webster J. G. (ed) 1988. Medical Instrumentation—Application and Design (John Wiley & Sons Inc, New York).). This standardisation is referred to as the 12-lead system, where each lead refers to a particular combination of electrode positions on the body and to the display of a specific signal derived from a combination of signals from these electrodes. Preferably, for the wristwatch style electrodynamic sensor monitoring system of the present specific embodiment, one sensor is worn on each wrist and the differential (left-right) signal is used for display. This is equivalent, in standard 12-lead terminology, to the I-lead electrocardiogram (defined as LA-RA) and is usually detected from electrodes placed on the shoulders or upper arms. The high fidelity of the present I-lead electrocardiogram taken from the finger tips or the wrists, is in part due to the non-invasive nature of the electrodynamic sensor and in part due to the high sensitivity and low noise of the electrometer amplifier used in its construction.

As well as applications in the clinical (ambulatory) monitoring of the I-lead electrocardiogram, this wristwatch style electrodynamic sensor also finds application in general heart rate monitoring. This variant of the electrodynamic sensor has two major advantages over current commercial, wristwatch style, rate monitors, used in the health and fitness fields.

Accurate monitoring of heart rate is essential in fitness training and the accuracy (in beats per minute) relies on how well a repeating feature (e.g. the QRS complex) can be identified and the accuracy with which the time between such features can be recorded. The accuracy of many commercial heart rate monitors is determined by comparing the measured rate with an electrocardiogram reference and it will be clear to one skilled in the art that the use of a sensor system which provides a high resolution electrocardiogram would give a more accurate determination of heart rate. The high sensitivity and non-invasive nature of the present electrodynamic sensor, with the capability of detecting at high resolution all the known features of an electrocardiogram (here from the wrists alone) would be ideal for this purpose.

Figure 23:
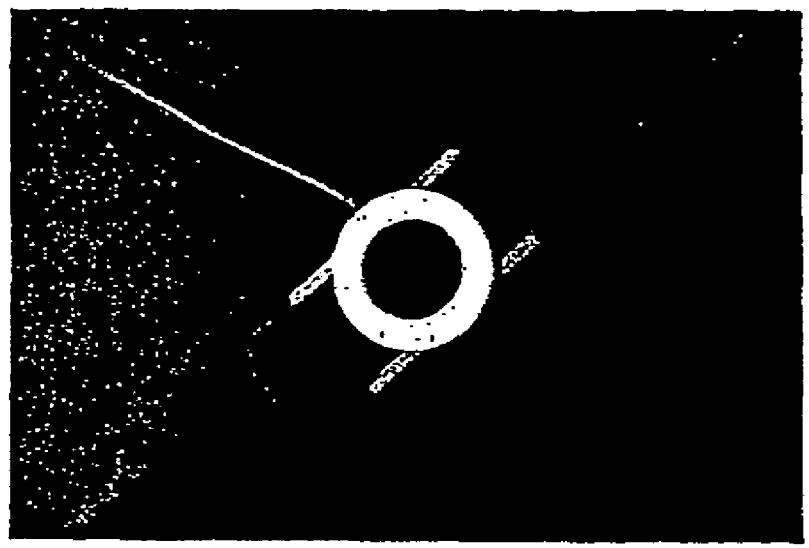
FIG. 23 is a photograph of a specific electrode.

A second advantage of using an electrodynamic sensor system over current heart rate monitors is one of comfort and convenience; In order to collect a heart signal with sufficient fidelity to be able to determine accurate rates, most commercial monitors use electrodes which are in cutaneous contact with the chest. The electric-potential-sensor-based wristwatch monitor of the present embodiment acts not just as the (non-invasive) electrode but also houses the first stage sensing and amplification electronics. The electrodynamic sensor is held firmly in place on the wrist by means of a suitable strap using hook and loop type fasteners. (See FIG. 23)

Figure 21:
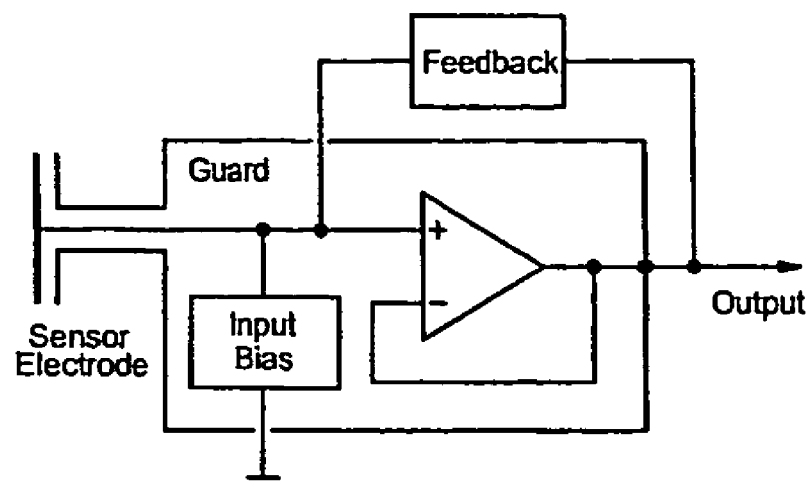
FIG. 21 is a block diagram of an electrodynamic sensor according to a particular embodiment of the invention.
Figure 22:
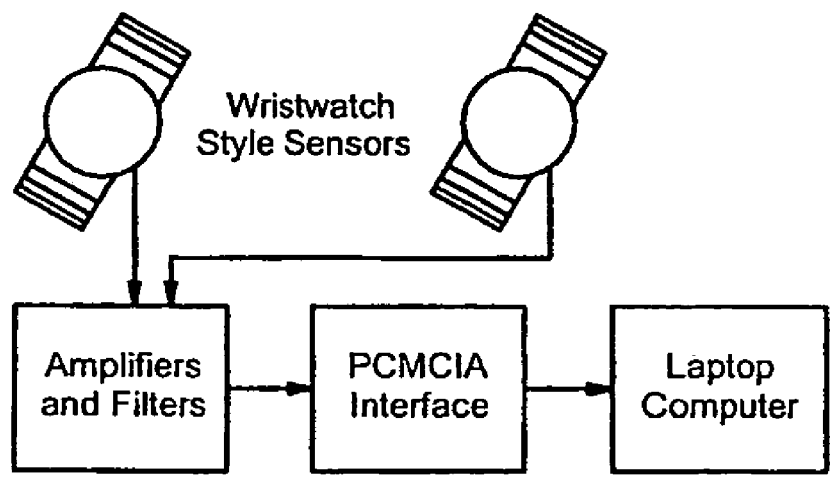
FIG. 22 is a schematic diagram of a particular aspect of the invention.

The electrodynamic sensor of the present invention, operates by detecting electric displacement current, rather than real charge current, so it does not require direct electrical contact to the source. It is therefore non-invasive in nature and completely biocompatible. It also has a extremely high input impedance ($10^{15}$ Ω at 1 Hz) and a very low noise floor (≈70 nV/√Hz at 1 Hz) which makes it ideal for electrocardiogram applications. The electrodynamic sensor is used in two electrically isolated configurations; a contact sensing mode and a remote off-body mode. In the contact mode, where the sensor is in mechanical contact with the body, single or multiple sensors are coupled via an appropriate sensor-body interface. In the remote mode, with an air-gap between the sensor and the body, fixed sensors are used which form a capacitive coupling to the body under measurement. A block diagram of a typical electrodynamic sensor is shown in FIG. 21. This shows a sensor electrode 21, having a guard 22, and an amplifier 23 with a feedback loop 24 from the output OP to the input IP. In this circuit system novel feedback techniques have been applied to a low noise electrometer amplifier in order to increase its effective input impedance and reduce its input capacitance. For ambulatory electrocardiogram and heart rate monitoring, the electrocardiogram signals are detected using two sensors, one attached to each of the subject's wrists. The system used for data acquisition and display is shown schematically in FIG. 22. Here, the voltage output from the two sensors 31, 32 is fed to a differential amplifier 33, followed by analogue filters 34 before being digitised and interfaced to a laptop computer 35 via a PCMCIA interface card 36. The system uses a 16-bit analogue-to-digital converter providing a voltage resolution of about 16 nV referred to the source. The sample rate used is typically 1000 samples/sec giving a time resolution of close to 1 ms. If required this sampling rate may be increased considerably (say, to ≈5000 to 10,000 samples/sec) with a concomitant improvement in time resolution. The whole system is powered from the mains or from batteries, as required. The wristwatch style electrodynamic sensor uses a 25 mm diameter active area and is attached by means of a standard 18 mm wide watchstrap, as shown in the photograph in FIG. 23. The active area of the sensor is electrically isolated from the body.

Figure 24:
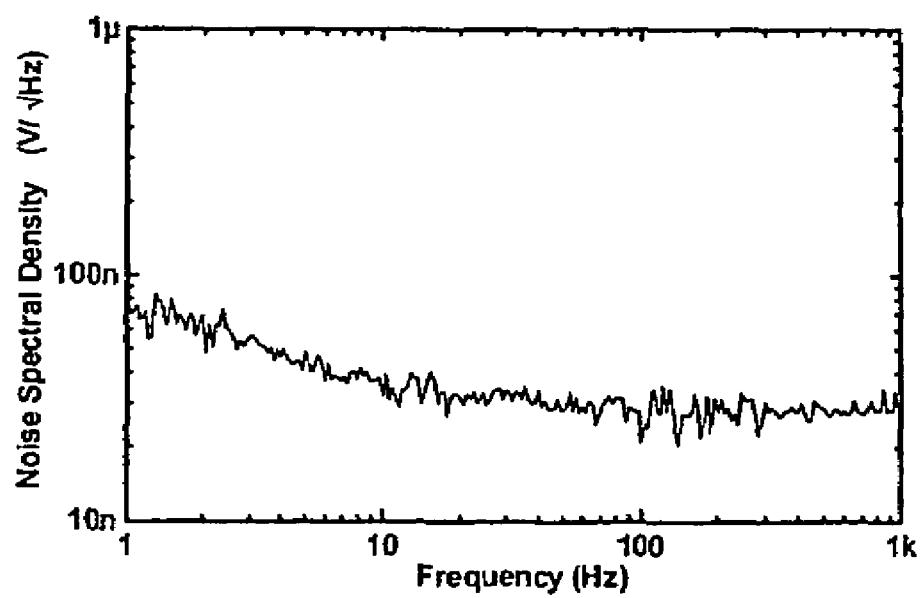
FIGS. 24 to 28 show data retrieved using the electrode of FIG. 23.
Figure 25:
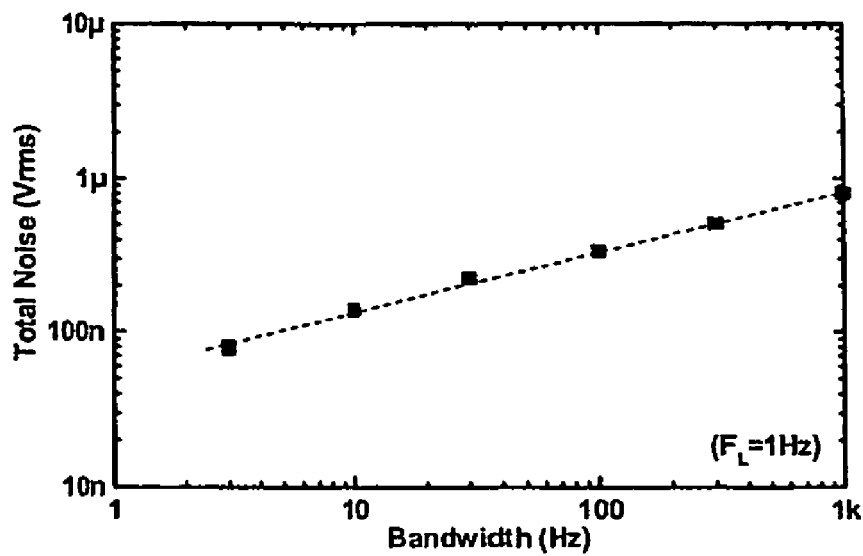

FIG. 24 shows the noise spectral density of a wristwatch style electrodynamic sensor in accordance with the present embodiment, indicating a noise floor of approximately 70 nV/√Hz at 1 Hz. While noise spectral density is a very good indicator of the noise floor as a function of frequency, it is often more useful to express the noise as the total noise in a given bandwidth. The total noise plotted against bandwidth is shown in FIG. 25. For a 30 Hz bandwidth (as used for obtaining the electrocardiograms in this embodiment) this total input referred noise is about 200 nV rms. To put this integrated noise in perspective, the amplitude of a normal QRS complex in a I-lead electrocardiogram is about 1 mV and the amplitude of the His bundle depolarisation at the skin surface is about 10-20 µV peak to peak.

Figure 26:
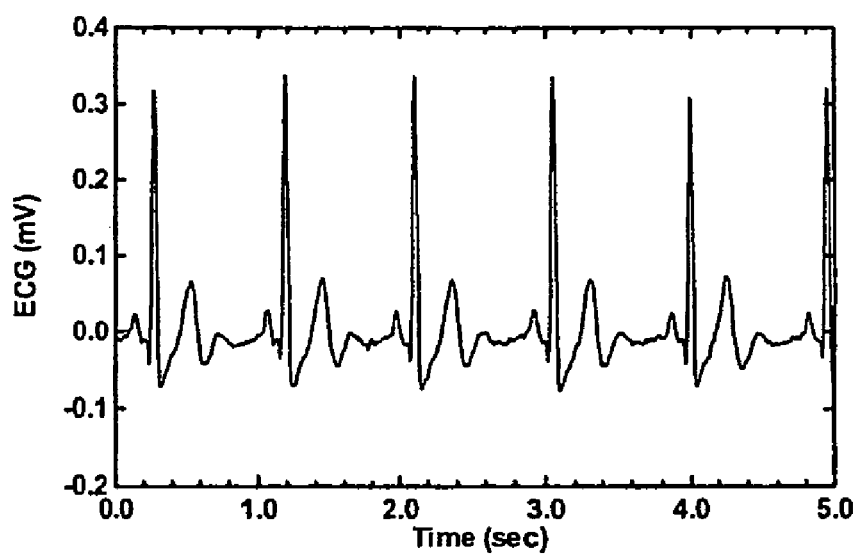
Figure 27:
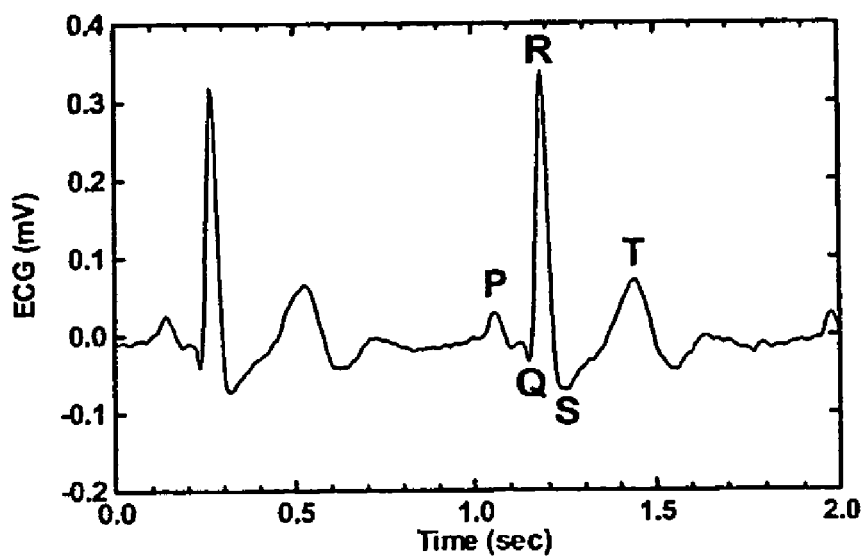

An example of a high resolution electrocardiogram obtained using a pair of electrodynamic sensors mounted in wristwatch style housings is shown in FIG. 26. This time domain signal is equivalent in cardiology terminology, to the I-lead, where the signal is derived from the difference between the two arm leads (LA-RA). In this case the I-lead is derived from the difference between the left and right wrist signals. The signal was recorded in real time in a bandwidth from 0.5 to 30 Hz, with no averaging or other electronic processing. The five seconds of data displayed in FIG. 26 contains five cardiac cycles and shows six QRS complexes. The heart rate is determined by measurement of the time periods between the R-peaks and in this case the average heart rate is 64 beats per minute. FIG. 27 shows a two-second period of an I-lead electrocardiogram obtained from a pair of wristwatch style electrodynamic sensors. This has all the usual features of a high-resolution electrocardiogram (the P wave, QRS complex and T wave). In addition, this electrocardiogram also contains features which are not usually seen in a conventional surface (signals detected on the surface of the body) electrocardiogram. These features (the H peak and the U wave), are labelled in FIG. 28 where approximately one cardiac cycle of the electrocardiogram is plotted (one second of data) with an expanded voltage scale to reveal the fine detail present in the waveform. The H peak corresponds in timing to the position of the His bundle depolarisation relative to the P and R features.

In clinical practice the depolarisation of the His bundle is customarily monitored using an electrode catheter inserted intravenously into the heart, the resultant time domain display being termed an intracardiac His bundle electrogram. In this intracardiac recording the A and V waves correspond, respectively, to the P wave and the QRS complex in the surface electrocardiogram. The H peak occurs between the A and V waves. In normal subjects the A-H interval is between 55 ms and 120 ms and the H-V interval is between 35 ms and 55 ms.

Figure 28:
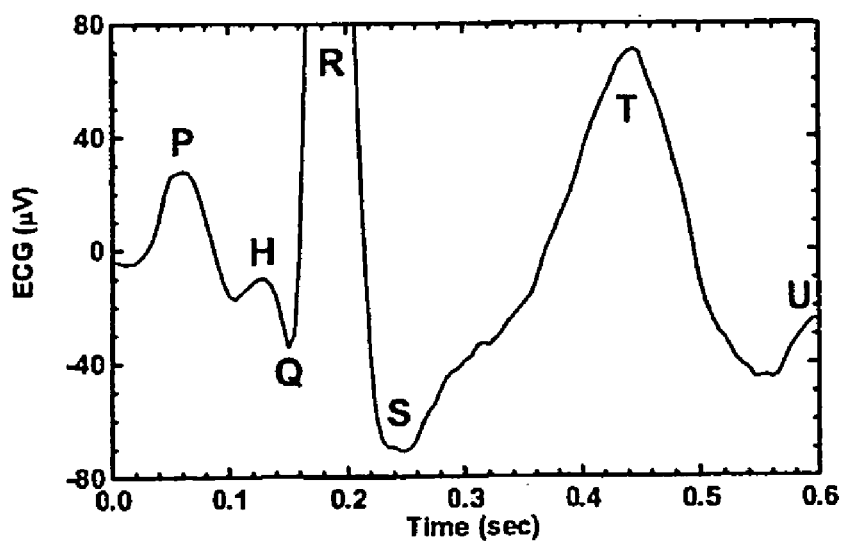

The measurement of the A-H and H-V intervals can indicate many varieties of heart disease. The A-H and H-V intervals cannot be measured from the surface electrocardiogram and the H peak has previously only been identified on the surface by using a large number of electrodes with spatial averaging of the resulting signals. By identifying the H-peak using the sensor described in this embodiment, we have extended the clinical capabilities of the surface electrocardiogram to more routine monitoring of the P-H (equivalent to A-H) and H-R (equivalent to H-V) intervals. The electrocardiogram shown in FIG. 28 gives a P-H interval of ≈70 ms and an H-R interval of ≈50 ms.

Figure 29:
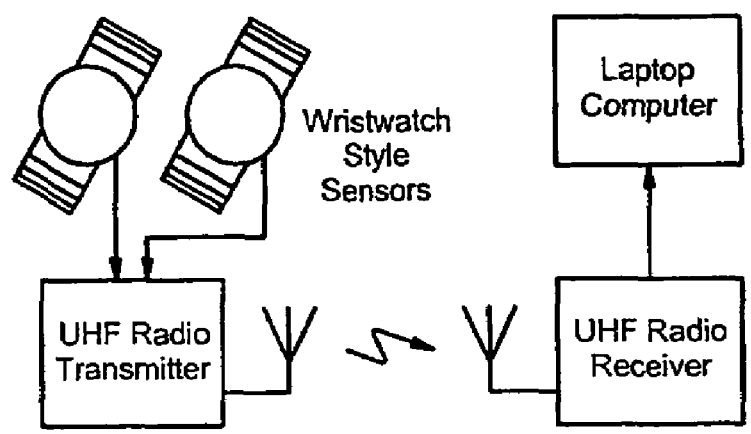
FIG. 29 is a block diagram of a further embodiment of the invention.
Figure 30:
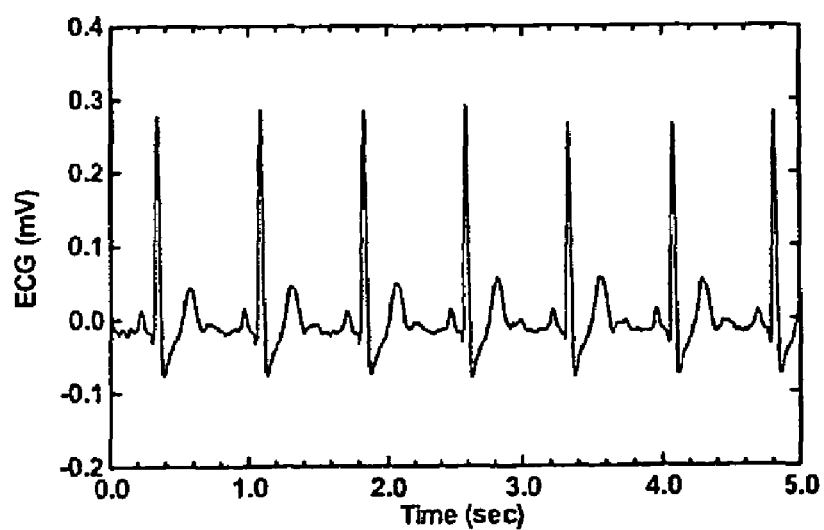
FIG. 30 shows data acquired using this apparatus.

Electrodynamic sensors in accordance with the present invention find particular application in remote telemetry. Conveniently, this may be achieved by physically separating the sensors 41, 42 from the following electronics 43 and display with the two sub-systems comprising a transmitter 44 and a receiver 45 coupled together by means of a radio link. Suitable, compact and inexpensive radio transmitters and receivers are available commercially from Low Power Radio Solutions, Quantec Group, U.K. Ltd. (Two Rivers Industrial Estate, Station Lane, Witney, Oxon, OX8 6BH).). These have been utilised in a specific embodiment to transmit the electrocardiogram waveforms (derived from the differentially configured electrodynamic sensors) from the body to a remote radio receiver and display system, as shown in the block diagram of FIG. 29. Here, the transmitter-receiver separation was typically 1 to 10 meters but it could be well over ten times this distance. The frequency modulated transmitter chosen had a centre (carrier) frequency of 418 MHz (ultra high frequency—UHF) and the sensors and transmitters were battery operated. FIG. 30 illustrates a typical electrocardiogram recorded using this monitoring system, taken at a sampling rate of 1000 samples/sec.

The sensitivity and low noise performance of electrodynamic sensors according to the invention permits their application to high spatial resolution (large number of elements) arrays which can be used to form real time images of the electrical activity of the heart. The man skilled in the art will readily substitute electrodynamic sensors of the present invention in place of conventional Ag/AgCl paste electrodes in standard (12-lead) electrocardiogram recording systems with reusable sensors held in position by a suitably designed harness or vest.

We have identified, in the surface electrocardiogram, a peak (H) which corresponds in timing to the position of the His bundle depolarisation. This feature is not visible in the standard surface electrocardiogram and has only been used clinically when monitored using an intracardiac electrode catheter inserted intravenously into the heart. Given the clinical importance of measuring the timing of the His bundle depolarisation relative to other features in the intracardiac recording, the ability to monitor this H peak in the surface electrocardiogram is of great benefit.

Inter alia, electrodynamic sensors in accordance with the present invention may advantageously be used in the following applications.

ECG—Long term ambulatory monitoring—using inert contact probes to provide improved patient comfort and to eliminate skin reaction
  Array imaging—linear or 2D arrays of sensors to provide spatio-temporal information by simultaneously obtaining data from many points
  Catheter probes—electrometer sensors may be built into catheter tubing for intravenous use, or a signal may be applied at the tip of an insulated catheter and the position located using a passive array of sensors EEG—Long term ambulatory monitoring—using inert contact probes to provide improved patient comfort and to eliminate skin reaction
  Array imaging—linear or two-dimensional arrays of sensors to provide spatio temporal information by simultaneously obtaining data from many points
  Machine interfaces—use of EEG signals to implement control functions directly and/or apply biofeedback
EOG—Machine interfaces—use of EOG signals to implement control functions directly and/or apply biofeedback e.g. computer games and vehicle control
Nerve muscle (EMG) and other biodynamic signals—
  Artificial limbs—use of sensors either singly or using multiple or array configurations to detect nerve and/or muscle signals and to implement control functions directly
  Robotics—remote sensing in either active or passive modes for proximity detection or control applications
  Machine interfaces—use of nerve and/or muscle signals to implement control functions directly and/or apply biofeedback
  Impedance tomography—using inductive or capacitive input signal coupling together with electrometer sensors an electrically isolated implementation of impedance tomography may be achieved
Remote sensing—
  Geophysical surveying—remote detection of potential gradients, dielectric anomalies and magnetotelluric signals of geological significance including the monitoring of ionospheric effects such as the Schumann resonance
  Crack and corrosion detection of metal structures—surface potential scans of metal surfaces to reveal defects via discontinuities in conductivity or current density caused by crack or corrosion defects in, for example, aircraft parts
  Motion detection—detection of movement of dielectric objects in a static electric field
  Earthquake prediction—monitoring of voltages generated by rocks under stress e.g. piezoelectric. Evidence exists indicating that piezoelectric signals may be precursors to major earthquake events.
Dielectric constant determination—
  Remote capacitive measurements—weak capacitative coupling may be used to determine the dielectric properties of materials including loss factor, without the problems due to electrode polarisation usually encountered with low frequency measurements
  Measurements of mixtures—capacitative measurements may be carried out on liquid systems or mixtures by immersion of insulating electrodes. By this method the dielectric properties may be determined without electrode polarisation problems. This is particularly applicable to, for example, mixtures of oil water and sand
Microscopic applications—
  Scanning IC surfaces—imaging of surface potentials above integrated circuits, yielding information about signal levels and real time propagation, DC biasing, dielectric properties and buried structures. Microprobes or arrays of microprobes may be fabricated to provide real time images
  Output transducer—use as a signal readout system which may be integrated into complex chips such as electro-optical devices and future quantum information processing and quantum computing systems
Remote neural network imaging—real time non-contact detection of signals and signal propagation within neural networks NMR NQR—the use of microprobes to detect the local time dependent electric field resulting from NMR or NQR. This technique avoids the cross talk usually encountered between the receive and transmit coils. High resolution imaging becomes easier using electric microprobes Single cell biology—electrical activity at the cellular level may be monitored using microprobes. Electrode polarisation is eliminated Single nerve/muscle fibre—monitoring of the electrical activity due to single nerve fibres may be accomplished using microprobes or arrays of microprobes. e.g. machine interfaces and control of artificial limbs Smart card—non-contact readout from smart card chips, which coupled with inductive or capacitive power and clock input signals would remove the necessity for direct electrical connections Body status monitoring—may include electrodes not in direct electrical contact but giving an output for the express purpose of monitoring awareness, sleep, or heart status of pilots, drivers or other persons performing critical functions. The output signals could also be used for biometric identification of individuals or to perform the function of a polygraph or lie detector.

It will be understood by those skilled in the art that an integrator may be substituted for a low-pass filter and that an active low-pass filter may be substituted for a passive low-pass filter. Discrete amplifiers may be employed in place of integrated circuit amplifiers.

Sensors in accordance with the invention may advantageously be from nano-scale upwards.

It will be apparent to one skilled in the art that the probes need not necessarily be identical.

Although the use of electrodynamic sensors has been described in relation to the measurement of electrocardiograms, electroencephologrames and the like, they may be adapted to the measurement of other electrical activity of a vital body.

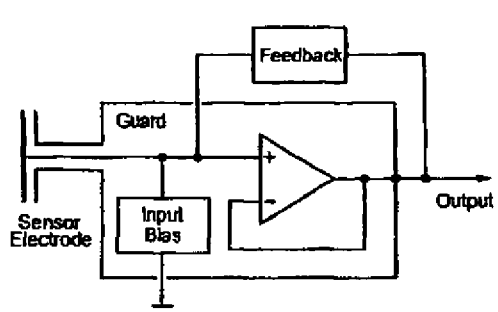

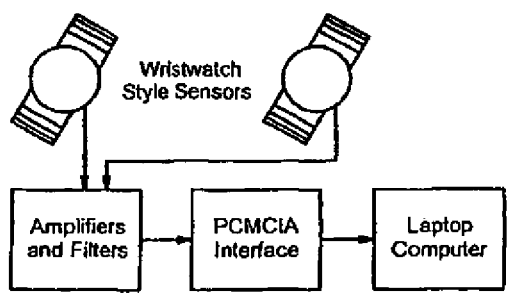

The invention claimed is:

1. An electrodynamic sensor comprising:
   an input probe for detecting small electrical potentials originating from an object under test and for generating detection signals, said input probe being configured for capacitive coupling with said object without direct electrical contact and comprising an electrode substrate having thereon a thin film of insulating material, and
   a high input impedance electrometer arranged to receive the detection signals and measure said electric potentials, the electrometer comprising:
   an amplifier,
   a dc input bias arrangement for providing a steady input bias current for said amplifier, said dc input bias arrangement including a biasing resistor,
   a dc to low frequency negative feedback loop comprising a low-pass filter circuit connected to receive amplified measurement signals and to feed a filtered stabilizing signal into the dc input bias arrangement for maintaining a stable dc operating point for the amplifier; and
   a combination of ancillary circuits configured cumulatively to increase the sensitivity of said electrometer to said small electrical potentials whilst not perturbing the electrical field associated therewith, the ancillary circuits including a guard circuit providing a shield surrounding said electrode substrate and input wiring for said amplifier, said guard circuit being driven by the output of the amplifier and being arranged to maintain the same potential on said one probe as on said shield, and a feedback arrangement between the output and the input of the amplifier, said feedback arrangement comprising a bootstrapping circuit for bootstrapping the biasing resistor of the dc input bias arrangement, and one of a neutralization circuit, a supply modulation circuit and an offset correction circuit for said amplifier.

2. An electrodynamic sensor according to claim 1 in which the feedback arrangement comprises at least bootstrapping and neutralization circuits.

3. An electrodynamic sensor according to claim 1 in which said one probe comprises a disc electrode, and in which said thin film of insulating material comprises an anodized oxide film.

4. An electrodynamic sensor according to claim 3 in which the thickness of said thin film is approximately 1 µm.

5. An electrodynamic sensor according to claim 3 in which the thickness of the oxide film is selected in dependence upon the surface area of the disc electrode and the material composing the disc electrode, in order to provide the capacitance required.

6. An electrodynamic sensor according to claim 1 in which said one probe comprises an electrode with a guarded coaxial structure.

7. An electrodynamic sensor according to claim 1 in which said one probe comprises a measurement electrode sandwiched between two guard planes in a tri-plate configuration.

8. An electrodynamic sensor according to claim 1 comprising a plurality of said probes configured as a linear or higher dimensional matrix array.

9. An electrodynamic sensor according to claim 1 in which said one probe is a scanning probe for scanning over a treatment area.

10. A method of sensing electrical activity comprising using the electrodynamic sensor according to claim 1.

11. An electrodynamic sensor according to claim 1 in which the electrometer further comprises a dc to low frequency negative feedback loop for feeding a stabilizing signal into the input bias arrangement for maintaining a dc operating point for the amplifier.

12. An electrodynamic sensor according to claim 11 in which the dc to low frequency negative feedback loop comprises a low-pass filter circuit for feeding a filtered signal into the input bias arrangement for maintaining a stable dc operating point for the amplifier.

13. An electrodynamic sensor according to claim 1 in which the amplifier is asymmetrically biased.

14. A wrist sensor comprising an the electrodynamic sensor according to claim 1, a sensor housing containing the sensor, wrist straps attached to the housing, and a strap fastening.

15. A biometric sensing system comprising the electrodynamic sensor according to claim 1 for non-invasive sensing of electrical activity of a vital body and for generating biometric measurement signals representing said electrical activity, and means for monitoring said biometric measurement signals.

16. A biometric sensing system according to claim 15 in which the sensor comprises multiple said probes arranged in a linear or higher dimensional array, and comprising processing means for producing dynamic potential line profiles or maps to measure or display the electrical activity on the surface of or from a location within the body.

17. A biometric sensing system according to claim 15 in which said one probe of said electrodynamic sensor is a scanning probe for scanning over a linear or higher dimensional area, and comprising processing means for producing dynamic potential line profiles or maps to measure or display the electrical activity on the surface of or from a location within the body.

18. A biometric sensing system according to claim 15 further comprising a transmitter arranged to transmit sensor output signals from the electrodynamic sensor, a receiver arranged to receive the transmitted signals, and a computer to which the receiver supplies such signals.

19. A body status monitor comprising the electrodynamic sensor according to claim 1 for generating body status measurement signals, and means for monitoring said body status measurement signals.

20. A biometric monitor for measuring biometric activity for generating one of electrocardiograms, electroencephalograms, electrooculograms and electromyograms, comprising the electrodynamic sensor according to claim 1 for generating biometric measurement signals, and means responsive to said biometric signals for recording and displaying said one of electrocardiograms, electroencephalograms, electrooculograms and electromyograms.

21. An array imaging device comprising the electrodynamic sensor according to claim 1, said sensor having an array of said probes, wherein the array of probes is arranged to provide measurement data from several points of the object, and imaging means for displaying said measurement data.

* * * * *

UNITED STATES PATENT AND TRADEMARK OFFICE
CERTIFICATE OF CORRECTION

| | |
|---|---|
| PATENT NO. | : 7,885,700 B2 |
| APPLICATION NO. | : 10/497813 |
| DATED | : February 8, 2011 |
| INVENTOR(S) | : Clark et al. |

It is certified that error appears in the above-identified patent and that said Letters Patent is hereby corrected as shown below:

<u>In Column 14</u>

Lines 34 – 43, (claims 11-12) please delete in their entirety.

Signed and Sealed this
Eighth Day of May, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,885,700 B2 | |
| APPLICATION NO. | : 10/497813 | |
| DATED | : February 8, 2011 | |
| INVENTOR(S) | : Clark et al. | |

It is certified that error appears in the above-identified patent and that said Letters Patent is hereby corrected as shown below:

Delete the title page and substitute therefore the attached title page showing the corrected number of claims in patent.

<u>In Column 14</u>

Lines 34 – 43, (claims 11-12) please delete in their entirety.

This certificate supersedes the Certificate of Correction issued May 8, 2012.

Signed and Sealed this
Twelfth Day of June, 2012

David J. Kappos
*Director of the United States Patent and Trademark Office*

CERTIFICATE OF CORRECTION (continued)

(12) United States Patent
Clark et al.

(10) Patent No.: US 7,885,700 B2
(45) Date of Patent: Feb. 8, 2011

(54) ELECTRODYNAMIC SENSORS AND APPLICATIONS THEREOF

(75) Inventors: Terence D. Clark, Lewes (GB); Robert J. Prance, Brighton (GB); Christopher J. Harland, Brighton (GB)

(73) Assignee: The University of Sussex, Brighton (GB)

( * ) Notice: Subject to any disclaimer, the term of this patent is extended or adjusted under 35 U.S.C. 154(b) by 1164 days.

(21) Appl. No.: 10/497,813

(22) PCT Filed: Dec. 9, 2002

(86) PCT No.: PCT/GB02/05560

§ 371 (c)(1), (2), (4) Date: Jul. 5, 2005

(87) PCT Pub. No.: WO03/048789

PCT Pub. Date: Jun. 12, 2003

(65) Prior Publication Data

US 2006/0058694 A1    Mar. 16, 2006

(30) Foreign Application Priority Data

Dec. 7, 2001 (GB) .................................. 0129390.1

(51) Int. Cl.
A61B 5/04 (2006.01)

(52) U.S. Cl. ........................................... 600/372
(58) Field of Classification Search .......... 600/372, 600/395; 607/116, 119
See application file for complete search history.

(56) References Cited

U.S. PATENT DOCUMENTS

| | | | |
|---|---|---|---|
| 3,500,823 A * | 3/1970 | Richardson et al. | 600/372 |
| 3,568,662 A * | 3/1971 | Everett et al. | 600/384 |
| 3,620,208 A * | 11/1971 | Higley et al. | 600/395 |
| 3,784,930 A | 1/1974 | Vosteen et al. | |
| 3,870,968 A | 3/1975 | Vosteen et al. | |
| 3,880,146 A * | 4/1975 | Everett et al. | 600/523 |
| 3,882,846 A * | 5/1975 | Fletcher et al. | 600/395 |

(Continued)

FOREIGN PATENT DOCUMENTS

EP    0 551 564    7/1993

(Continued)

OTHER PUBLICATIONS

L. N. Hulley, D. Robson: High input impedance circuits for the measurement of bioelectric potentials Journal of Scientific Instruments, vol. 43, No. 10, Oct. 1996 pp. 728-734.

(Continued)

Primary Examiner — George R Evanisko
(74) Attorney, Agent, or Firm — Locke Lord Bissell & Liddell

(57) ABSTRACT

An electrodynamic sensor comprises a high input impedance electrometer adapted to measure small electrical potentials originating from an object under test and having a pair of input probes, characterized in that at least one of said pair of input probes has no direct electrical contact with said object, wherein the circuit arrangement of said electrometer comprises an amplifier which includes a combination of ancillary circuits cumulatively to increase the sensitivity of said electrometer to said small electrical potentials whilst not perturbing the electrical field associated therewith.

19 Claims, 18 Drawing Sheets